US005945102A

United States Patent [19]
de Faire et al.

[11] Patent Number: 5,945,102
[45] Date of Patent: Aug. 31, 1999

[54] CRUSTACEAN AND FISH DERIVED MULTIFUNCTIONAL ENZYME

[75] Inventors: Johan R. de Faire, Vattholma, Sweden; Richard L. Franklin, London; John Kay, Cardiff, both of United Kingdom; Ragnvald Lindblom, Muang Rayong, Thailand

[73] Assignee: Phairson Medical Inc., London, United Kingdom

[21] Appl. No.: 08/385,540

[22] Filed: Feb. 8, 1995

Related U.S. Application Data

[63] Continuation-in-part of application No. 08/338,501, Nov. 22, 1994, abandoned.

[51] Int. Cl.⁶ .......................... A61K 38/46; A61K 38/48; A61K 38/54; C12P 37/02
[52] U.S. Cl. .................... 424/94.63; 424/94.2; 424/94.6; 424/94.64; 435/226
[58] Field of Search .............................. 424/94.63, 94.6, 424/94.1, 94.2, 94.64; 435/226, 264, 267, 268

[56] References Cited

U.S. PATENT DOCUMENTS

| | | | |
|---|---|---|---|
| 4,677,069 | 6/1987 | Chen et al. | 435/226 |
| 4,801,451 | 1/1989 | Hellgren et al. | 424/94.63 |
| 4,963,491 | 10/1990 | Hellgren et al. | 435/264 |
| 5,134,119 | 7/1992 | John et al. | 514/8 |
| 5,439,935 | 8/1995 | Rawlings et al. | 514/451 |

FOREIGN PATENT DOCUMENTS

| | | |
|---|---|---|
| 170 115 A1 | 7/1985 | European Pat. Off. . |
| 61-68419 | 4/1986 | Japan . |
| WO 93/19732 | 10/1993 | WIPO . |
| 93/24142 | 12/1993 | WIPO . |
| WO 94/19005 | 9/1994 | WIPO . |
| WO 95/07686 | 3/1995 | WIPO . |
| WO 95/07688 | 3/1995 | WIPO . |

OTHER PUBLICATIONS

Grant et al., Amino Acid Sequence of a Collagenolytic Protease from the Hepatopancreas of the Fiddler Crab, *UCA Pugilator,* Biochemistry, 19:4653–4659 (1980).
Grant and Eisen, Substrate Specificity of the Collagenolytic Serine Protease from *UCA Pugilator:* Studies with Noncollagegenous Substrates, Biochemistry, 19:6089–6095 (1980).
Grant et al., Collagenolytic Protease from Fiddler Crab (*UCA Pugilator*), Methods in Enzymology, 80:722–734 (1980).
Welgus et al., Substrate Specificity of the Collagenolytic Serine Protease from *UCA Pugilator:* Studies with Collagenous Substrates, Biochemistry, 21:5183–5189 (1982).
Grant et al., A Collagenolytic Serine Protease with Trypsin–Like Specificity from the Fiddler Crab *UCA Pugilator,* Biochemistry, 22:354–358 (1983).
Welgus and Grant, Degradation of Collagen Substrates by a Trypsin–Like Serine Protease from the Fiddler Crab *UCA Pugilator,* Biochemistry, 22:2228–2233 (1983).

Al–Mohanna et al., Mitotic E– and Secretory F–Cells in the Hepatopancreas of the Shrimp *Penaeus Semisulcatus* (Crustacea: Decapoda), J. Mar. Biol. Ass. U.K., 65:901–910 (1985).
Lipman and Pearson, Rapid and Sensitive Protein Similarity Searches, Science, 227:1435–1441 (Mar. 22, 1985).
Gudmundsodottir et al., Isolation and Characterization of cDNAS from Atlantic Cod Encoding Two Different Forms of Trypsinogen, Eur. J. Biochem., 217, 1091–1097 (1993).
Lu et al., The Midgut Trypsins of Shrimp (*Penaeus Monodon*), Biol. Chem. Hoppe–Seyler, 371:851–859 (Sep. 1990).
Turkiewicz et al., Collagenolytic Serine Proteinase from *Euphausia Superba Dana* (Antartic Krill), Comp. Biochem. Physiol., 99B:359–371 (1991).
Tsai et al., The Midgut Chymotrypsins of Shrimps (*Penaeus Mondon, Penaeus Japonicus* and *Penaeus Penicillatus*) Biochimica et Biophysica Acta, 1080:59–67 (1991).
Wormhoudt et al., Purfication, Biochemical Characterization and N–Terminal Sequence of a Serine–Protease with Chymotrypsic and Collagenolytic Activities in a Tropical Shrimp, *Penaeus Vannamei* (Crustacea, Decapoda), Comp. Biochem. Physiol., 103B(3):675–680 (1992).
Sellos and Wormhoudt, Molecular Cloning of a cDNA That Encodes a Serine Protease with Chymotryptic and Collagenolytic Activities in the Hepatopancreas of the Shrimp *Penaeus Vanameii* (Crustacea, Decapoda), FEBS, 309(3):219–224 (Sep. 1992).
Klimova et al., The Isolation and Properties of Collagenolytic Proteases from Crab Hepatopancreas, Biochemical and Biophysical Research Communications, 166(3):1411–1420 (Feb. 1990).
Tsu et al., The Substrate Specificity of *UCA Pugilator* Collagenolytic Serine Protease 1 Correlates with the Bovine Type I Collagen Cleavage Sites, The Journal of Biochemical Chemistry, 269(30)19565–19572 (1994).

(List continued on next page.)

Primary Examiner—Donna C. Wortman
Assistant Examiner—Jay Williams
Attorney, Agent, or Firm—Dechert Price & Rhoads

[57] ABSTRACT

The invention relates to a multifunctional enzyme that can be derived from crustaceans or fish. The enzyme has at least one of a chymotrypsin, trypsin, elastase, collagenase and exo peptidase activity, and a molecular weight between about 20 kd and about 40 kd. Preferably, the multifunctional enzyme has substantial anti cell-cell adhesion activity. Preferably, the multifunctional enzyme has substantial homology with the krill multifunctional enzyme. These enzymes are useful for treating viral infections such as herpes outbreaks, fungal, bacterial or parasitic infections, including the primary and secondary infections of leprosy, colitis, ulcers, hemorrhoids, corneal scarring, dental plaque, acne, cystic fibrosis, blood clots, wounds, immune disorders including autoimmune disease and cancer. Additionally, the invention relates to a method of purifying the multifunctional enzyme, and to a preparation of essentially purified multifunctional enzyme.

12 Claims, 9 Drawing Sheets

OTHER PUBLICATIONS

B. Johansson et al., Purification and Identification of Carboxy–Peptidase A and B from Antarctic Krill (*Euphausia Superba*), Biol. Chem. Hoppe Sryler, 367:366, Abstract 06.03.56 (1986).

A. Bucht et al., Immunological Characterization of Three Highly Purified Trypsin–Like Enzymes from Antarctic Krill (*Euphausia Superba*), Biol. Chem. Hoppe Sryler, 367:366, Abstract 06.03.55 (1986).

Turkiewicz et al., Purification and Characterization of a Proteinase from *Euphausia Superba Dana*(Antarctic Krill), Acta Biochimica Polonica, 33(2):87–89 (1986).

Chen et al., Purification and Properties of Trypsin–Like Enzymes and a Carboxypeptidase A from *Euphausia Superba*, Journal of Food Biochemistry, 2:349–366 (1978).

Kimoto et al., Purification and Characterization of Serine Proteinases from *Euphasia Superba*, Agric. Biol. Chem., 47(3):529–534 (1983).

Kimoto et al., Purification and Characterization of Chymotrypsin–Like Proteinase from *Euphausia Superba*, Agric. Biol. Chem., 49(6):1599–1603 (1985).

Knut Kr. Osnes et al., On the Purification and Characterization of Three Anoinic, Serine–Type Peptide Hydrolases from Antartic Krill, *Euphausia Superba*, Comp. Biochem. Physiol., 82B(4):607–619 (1995).

Knut Kr. Osnes et al., On the Purification and Characterization of Exopeptidases from Antarctic Krill, *Euphasia Superba*, Comp. Biochem. Physiol., 83B(2):445–458 (1986).

Knut Kr. Osnes et al., Hydrolysis of Proteins by Peptide Hydrolases of Antartic Krill, *Euphausia Superba*, Comp. Biochem. Physiol., 83B(4):801–805, (1986).

Knut Kr. Osnes et al., Peptide Hydrolases of Antartic Krill, *Euphausia Superba*, Comp. Biochem. Physiol, 82B(4):599–606, (1985).

Olav Seather et al., Proteolysis Post Mortem in North Atlantic Krill, Comp. Biochem. Physical, 88B(1):165–176 (1987).

Dialog Search relating to enzyme–based therapeutics.

J. Melrose et al., Evaluation of Digestive Proteinases from the Antarctic Krill *Euphasia Superba* as Potential Chemonucleolytic Agents, Arch Orthop Trauma Surg., 114:145–152 (1995).

Y. Sakharov, Potent Debriding Ability of Collagenolytic Protease Isolated from the Hepatopancreas of the King Crab *Paralithodes Camtschatica*, Arch Dermatol Res., 285:32–35 (1993).

Arthur Z. Eisen, A Collagenolytic Protease from the Hepatopancreas of the Fiddler Crab, *UCA Pugilator*, Purification and Properties, Biochemistry, 12(9):1814–1822 (1973).

Asuncion Olalla et la., Purification and Properties of Three Proteases from the Larvae of the Brine Shrimp *Artemia Salina*, Biochimica et Biophysica Acta, 523:181–190 (1978).

Spindler et al., Partial Characterization of Chitin Degrading Enzymes from Two Euphausiids, *Euphausia Superba* and *Meganyctiphanes Norvegica*, Polar Biology, 9:115–122 (1988).

Karlstam and Ljunglof, Detection and Partial Purification of a Hyaluronic Acid–Degrading Enzyme from Antarcic Krill (*Euphausia Superba*), Biol. Chem. Hoppe Seyler, 367:339 (1986).

Kimoto et al., Acid Proteinases from Antartic Krill, *Euphausia Superba*: Partial Purification and Some Properties, Journal of Food Science, 46:1881–1884 (1981).

Kraft and Falkenberg, Biol. Chem. Hoppe Seyler, 353:1540–1541 (1972).

Anheller et al., Biochemical and Biological Profile of a New Enzyme Preparation from Antarctic Krill (*E. Superba*) Suitable for Debridemen of Ulcerative Lesions, Archives of Dermatology Research, 281:105–110 (1989).

Sakharov et al., Purification and Characterization of Two Serine Collagenolytic Proteases from Crab *Paralithodes Camtschatica*, Comp. Biochem. Physiol., 108B:561–568 (1994).

Gates et al., Isolation of Comparative Properties of Shrimp Trypsin*, Shrimp Trypsin, 8(11):4483–4489 (1969).

Dialog Search relating to cysteine protease.

Von P. Billigmann, Fortschrr Med., 113(4):43–48 (1995) [German].

Theodor Nasemann et al., Hautarz, 18(1):31–35 (1967) [German].

V. Mazza, Folia Med., 52(9):565–578 (1969) (Napoli).

Berenshtein, Antibiotiki, 23(11):1002–1005 (1978) [German].

Daniushchenkova, Antibiotiki, 23(4):330–333 (1978) [German].

C. D'Arrigo, Minerva Medica, 60(87):4327–4334 (1969) [Italian].

Poul Kjer, Nordisk Medicin, 75(14):390–391 (1966) [?? ].

Gastshchev, Sovetskaia Meditsina, (9):52–56 (1980) [German].

Gotishchev, Sovetskaia Meditsina, (5):80–83 (1978) [German].

DiMarco, Clin Pediatr, (Bologna), 52(1):34–45 (1970) [Italian].

Tokuda, Nippon Ganka Kiyo, 19(10):993–998 (1968) [Japanese].

Jacobs, J Am Podiatry Assoc., 55(11):743–746 (1965) [English].

Goodfriend, J Am Podiatry Assoc., 55(9):667–669 (1965) [English].

Chudakov, Kirurgiia (Mosk), 49(2):87–91 (1973) [Russian].

Geller, Khirurgiia (Mosk), 49(2):64–65 (1973) [Russian].

Demianiuk, Klin Khir, 8:56–60 (1972) [Russian].

Grigorian, Klin Khir, 9:1–4 (1971) [Russian].

Bar, Lille Med., 15(5):827–847 (1970) [French].

Riffat, Lyon Med., 226(13):103–106 (1971) [French].

Gacon, Lyon Med., 222(43):997–1000 (1969) [French].

Bazerque, Medicina (B. Aires), 32(4):357–362 (1972) [Spanish].

Gordillo Fernandez, Medicina (Mex), 45(973):490–493 (1965) [Spanish].

Lopez Reyes, Medicina (Mex), 45(964):221–223 (1965) [Spanish].

Athie, Medicina (Mex), 45(961):145–150 (1965) [Spanish].

Zhailiev DS, Khirurgiia (Mosk), (1):67–70 (1984) [Russian].

Szeghy, Klin Monatshl Augenheilkd, 153(6):827–830 (1968) [German].

Rathgeber WF, S. Afr. Med. J., (45(7):181–183 (1971) [English].

Coblentz, J. Am. Geriatr Soc., 16(9):1039–1046 (1968) [English].

V.N. Glozman, (10):57–59 (1990) [Russian].

T.K. Chuchnova, (10):52–55 (1990) [Russian].

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear (xi) SEQUENCE DESCRIPTION: SEQ ID NO:1:

Ile Val Gly Gly Asn Glu Val Thr Pro His Ala Tyr Pro Trp Gln Val
1               5                   10                  15

Gly Leu Phe Ile Asp Asp Met Tyr Phe
            20                  25

(2) INFORMATION FOR SEQ ID NO:2:

(i) SEQUENCE CHARACTERISTICS:
      (A) LENGTH: 25 amino acids
      (B) TYPE: amino acid
      (C) STRANDEDNESS: single
      (D) TOPOLOGY: linear (xi) SEQUENCE DESCRIPTION: SEQ ID NO:2:

```
Ile Val Gly Gly Met Glu Val Thr Pro His Ala Tyr Pro Trp Gln Val
 1               5                  10                  15

Gly Leu Phe Ile Asp Asp Met Tyr Phe
            20                  25
```

(2) INFORMATION FOR SEQ ID NO:3:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:3:

```
Ile Val Gly Gly Val Glu Ala Thr Pro His Ser Trp Pro His Gln Ala
 1               5                  10                  15

Ala Leu Phe Ile Asp Asp Met Tyr Phe
            20                  25
```

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:4:

```
Ile Val Gly Gly Val Glu Ala Thr Pro His Ser Xaa Pro His Gln Ala
 1               5                  10                  15

Ala Leu Phe Ile
            20
```

(2) INFORMATION FOR SEQ ID NO:5:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:5:

```
Ile Val Gly Gly Thr Ala Val Thr Pro Gly Glu Phe Pro Tyr Gln Leu
 1               5                  10                  15

Ser Phe Gln Asp Ser Ile Glu Gly Val
            20                  25
```

(2) INFORMATION FOR SEQ ID NO:6:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:6:

```
Ile Val Gly Gly Val Glu Ala Val Pro Gly Val Trp Pro Tyr Gln Ala
 1               5                  10                  15

Ala Leu Phe Ile Ile Asp Met Tyr Phe
            20                  25
```

(2) INFORMATION FOR SEQ ID NO:7:

(i) SEQUENCE CHARACTERISTICS:
        (A) LENGTH: 25 amino acids

```
            (B) TYPE: amino acid
            (C) STRANDEDNESS: single
            (D) TOPOLOGY: linear (xi) SEQUENCE DESCRIPTION: SEQ ID NO:7:

Ile Val Gly Gly Val Glu Ala Val Pro His Ser Trp Pro Tyr Gln Ala
 1               5                  10                  15

Ala Leu Phe Ile Ile Asp Met Tyr Phe
            20                  25

(2) INFORMATION FOR SEQ ID NO:8:

(i) SEQUENCE CHARACTERISTICS:
            (A) LENGTH: 25 amino acids
            (B) TYPE: amino acid
            (C) STRANDEDNESS: single
            (D) TOPOLOGY: linear (xi) SEQUENCE DESCRIPTION: SEQ ID NO:8:

Ile Val Gly Gly Val Glu Ala Val Pro Asn Ser Trp Pro His Gln Ala
 1               5                  10                  15

Ala Leu Phe Ile Asp Asp Met Tyr Phe
            20                  25

(2) INFORMATION FOR SEQ ID NO:9:

(i) SEQUENCE CHARACTERISTICS:
            (A) LENGTH: 20 amino acids
            (B) TYPE: amino acid
            (C) STRANDEDNESS: single
            (D) TOPOLOGY: linear (xi) SEQUENCE DESCRIPTION: SEQ ID NO:9:

Ile Val Gly Gly Gln Asp Ala Thr Pro Gly Gln Phe Pro Tyr Gln Leu
 1               5                  10                  15

Ser Phe Gln Asp
            20

(2) INFORMATION FOR SEQ ID NO:10:

(i) SEQUENCE CHARACTERISTICS:
            (A) LENGTH: 19 amino acids
            (B) TYPE: amino acid
            (C) STRANDEDNESS: single
            (D) TOPOLOGY: linear (xi) SEQUENCE DESCRIPTION: SEQ ID NO:10:

Ile Val Gly Gly Gln Glu Ala Ser Pro Gly Ser Trp Pro Xaa Gln Val
 1               5                  10                  15

Gly Leu Phe (2) INFORMATION FOR SEQ ID NO:11:

(i) SEQUENCE CHARACTERISTICS:
            (A) LENGTH: 20 amino acids
            (B) TYPE: amino acid
            (C) STRANDEDNESS: single
            (D) TOPOLOGY: linear (xi) SEQUENCE DESCRIPTION: SEQ ID NO:11:

Ile Val Gly Gly Gln Glu Ala Ser Pro Gly Ser Trp Pro Xaa Gln Val
 1               5                  10                  15

Gly Leu Phe Phe
            20
```

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:12:

Ile Val Gly Gly Thr Glu Val Thr Pro Gly Glu Ile Pro Tyr Gln Leu
1               5                   10                  15

Ser Leu Gln Asp
            20

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:13:

Ile Val Gly Gly Thr Glu Val Thr Pro Gly Glu Ile Pro Tyr Gln Leu
1               5                   10                  15

Ser Phe Gln Asp
            20

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:14:

Ile Val Gly Gly Ser Glu Ala Thr Ser Gly Gln Phe Pro Tyr Gln Xaa
1               5                   10                  15

Ser Phe Gln Asp
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:15:

Ile Val Gly Gly Thr Asp Ala Thr Leu Gly Glu Phe Pro Tyr Gln Leu
1               5                   10                  15

Ser Phe Gln Asn
            20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:16:

Ile Val Asn Gly Glu Asp Ala Val Pro Gly Ser Trp Pro Trp Gln Val
1               5                   10                  15

```
Ser Leu Gln Asp
         20

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:17:

Ile Val Gly Gly Xaa Glu Val Thr Pro His Ala Tyr Pro Trp Gln Val
 1               5                  10                  15

Gly Leu Phe Ile Asp Asp Met Tyr Phe
            20                  25

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:18:

Ile Val Gly Gly Tyr Glu Cys Lys Ala Tyr Ser Gln Ala Tyr Gln Val
 1               5                  10                  15

Ser Leu Asn Ser Gly Tyr His Tyr Cys
            20                  25

(2) INFORMATION FOR SEQ ID NO:19:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:19:

Ile Val Gly Gly Tyr Glu Cys Thr Lys His Ser Gln Ala His Gln Val
 1               5                  10                  15

Ser Leu Asn Ser Gly Tyr His Tyr Cys
            20                  25

(2) INFORMATION FOR SEQ ID NO:20:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:20:

Ile Val Gly Gly Tyr Glu Cys Thr Arg His Ser Gln Ala His Gln Val
 1               5                  10                  15

Ser Leu Asn Ser Gly Tyr His Tyr Cys
            20                  25
```

CRUSTACEAN AND FISH DERIVED MULTIFUNCTIONAL ENZYME

This application is a continuation-in-part of U.S. application Ser. No. 08/338,501, filed Nov. 22, 1994, now abandoned, titled "Enzyme Composition from Antarctic Krill".

The present invention relates to the discovery that there exists a family of crustacean and fish derived enzymes having substantial structural similarity to an enzyme derived from antarctic krill. The krill enzyme is the subject of U.S. patent application Ser. No. 08/338,501, filed Nov. 22, 1994, which is the national-stage application for PCT/SE93/00455, filed May 21, 1993, which claims the priority Swedish Application No. 9201628-6, filed May 22, 1992. The entire disclosure of U.S. patent application Ser. No. 08/338,501, is incorporated herein by reference. These related enzymes are believed to have the same utility as the krill enzyme. In particular, these enzymes are useful for treating viral infections such as herpes outbreaks, fungal, bacterial or parasitic infections, including the primary and secondary infections of leprosy, colitis, ulcers, hemorrhoids, corneal scarring, dental plaque, acne, cystic fibrosis, blood clots, wounds, immune disorders including autoimmune disease and cancer. Additionally, the invention relates to a method of purifying the multifunctional enzyme, and to a preparation of essentially purified multifunctional enzyme.

U.S. Pat. Nos. 4,801,451 and 4,963,491 disclose a mixture of exo- and endopeptidases isolated from antarctic krill (*Euphasia superba*) and the use of the mixture as cleaning solutions. U.S. Pat. No. 4,801,451 discloses the use of such enzymes to remove foreign matter and dead tissue from wounds.

Patent Application WO 85/04809 discloses the use of krill enzymes as a digestion promotor. European Application EP-A1-0170115 discloses the use of krill enzymes to dissolve blood clots.

Isolations and partial sequences of various fish or crustacean proteases have been reported. A number of such reports are identified in Table 1, below.

TABLE 1

Sequence Reports

*Penaeus vanamelii* 1

| | |
|---|---|
| Sequence reported: | Van Wormoudt et al., Comp Biochem. Physiol., 103B: 675–680, 1992 and Sellos and Wormhoudt, FEBS, 39: 219–224, 1992. |
| Reported activities: | chymotryptic |
| Apparent MW: | 25 kd |

*Panaeus vanameii* 2

| | |
|---|---|
| Sequence reported: | Van Wormoudt et al., Comp Biochem. Physiol., 103B: 675–680, 1992. |
| Reported activities | chymotryptic (tryptic) |
| Apparent MW: | 25 kd |

*Panaeus monodon tryptic* (shrimp)

| | |
|---|---|
| Sequence reported: | Lu et al., Biol. Chem. Hoppe-Seyler, 371: 851–859, 1990. |
| Reported activities: | tryptic |
| Apparent MW: | 27 kd |
| Ph optimum: | 7.4–8.0 |
| Pi: | ≤2.4 |

*Panaeus monodon*

TABLE 1-continued

Sequence Reports chymotryptic - 1 (shrimp)

| | |
|---|---|
| Sequence reported: | Tsai et al., Biochem et Biophys. Acta, 1080: 59–67, 1991 |
| Reported activities: | chymotryptic collagenase |
| Apparent MW: | 27–28 kd |

*Panaeus monodon* chymotryptic - 2

| | |
|---|---|
| Sequence reported: | Tsai et al., Biochem. et Biophys. Acta, 1080: 59–67, 1991 |
| Reported activities: | chymotryptic collagenase |
| Apparent MW: | 25–26 kd |

*Uca pubilator* (Fiddler Crab) 1

| | |
|---|---|
| Sequence reported: | Grant et al., Biochemistry, 19: 4653–4659, 1980. |
| Reported activities: | chymotryptic |
| Apparent MW: | 25 kd |
| Ph optimum | 8.0–8.5 |

*Uca pugilator* II

| | |
|---|---|
| Sequence reported: | Grant et al., Biochemistry, 19: 4653–4659, 1980. |
| Reported activities: | chymotryptic collagenase |
| Apparent MW: | 25 kd |
| pI: | 8.0–8.5 |

Kamchatka crab (at least four proteases)

| | |
|---|---|
| Sequence Reported: | Klimova et al., Biochem. Biophys. Res. Commun. 166: 1411–1420, 1990 |
| Reported Activities: | tryptic collagenase |
| Apparent MW: | 23–26 kd |

Crayfish Protease

| | |
|---|---|
| Sequence reported: | Titani et al., Biochemistry, 22: 1459–1465, |

A krill-derived protease has now been purified to a high degree of purity. The purified protease has apparent MW of about 29 kd, pI of about 4.0, and displays chymotrypsin, trypsin, elastase, collagenase and exo peptidase activity. The sequence of the first 25 amino acids is I-V-G-G-N/M-E-V-T-P-H-A-Y-P-(W)-Q-V-G-L-F-I-D-D-M-Y-F (SEQ ID NO:17). The parentheses indicate a weak recovery of the 14th amino acid and "N/M" indicates heterogeneity at the 5th position. A comparison of the N-terminal 20 to 25 amino acid sequences of various serine proteases is presented in Table 2, below.

TABLE 2

N-Terminal Sequences

| Species | SEQ ID NO | Sequence |
|---|---|---|
| Penaeus vanameii 1 (shrimp) | 3 | I V G G V E A T P H S W P H Q A A L F I D D M Y F |
| Penaeus vanameii 2 | 4 | I V G G V E A T P H S X P H Q A A L F I |
| P. monodon, trypt. (shrimp) | 5 | I V G G T A V T P G E F P Y Q L S F Q D S I E G V |
| P. monodon, chym. 1 | 6 | I V G G V E A V P G V W P Y Q A A L F I I D M Y F |
| P. monodon, chym. 2 | 7 | I V G G V E A V P H S W P Y Q A A L F I I D M Y F |
| Uca pugilator I (crab) | 8 | I V G G V E A V P N S W P H Q A A L F I D D M Y F |
| Uca pugilator II | 9 | I V G G Q D A T P G Q F P Y Q L S F Q D |
| King crab | 10 | I V G G Q E A S P G S W P ? Q V G L F |
| Kamchatka crab IA | 11 | I V G G Q E A S P G S W P X Q V G L F F |
| IIA | 12 | I V G G T E V T P G E I P Y Q L S L Q D |
| IIB | 13 | I V G G T E V T P G E I P Y Q L S F Q D |
| IIC | 14 | I V G G S E A T S G Q F P Y Q X S F Q D |
| Crayfish | 15 | I V G G T D A T L G E F P Y Q L S F Q N |
| krIII Enzyme | 1 | I V G G N E V T P H A Y P W Q V G L F I D D M Y F |
| | 2 | I V G G M E V T P H A Y P W Q V G L F I D D M Y F |
| Bovine chymotrypsin | 16 | I V N G E D A V P G S W P W Q V S L Q D |
| Salmon | 18 | I V G G Y E C K A Y S Q A Y Q V S L N S G Y H Y C |
| Atlantic Cod | 19 | I V G G Y E C T K H S Q A H Q V S L N S G Y H Y C |
| Atlantic Cod | 20 | I V G G Y E C T R H S Q A H Q V S L N S G Y H Y C |

X = unknown or undefined.

The invention relates to a multifunctional enzyme that can be derived from crustaceans or fish. The enzyme has at least one of a chymotrypsin, trypsin, elastase, collagenase and exo peptidase activity such as both an endo- and exo peptidase activity, and a molecular weight between about 20 kd and about 40 kd in one embodiment the enzyme has molecular weight of 26,000–32,000. Preferably, the enzyme has at least two of the identified proteolytic activities, more preferably at least three, still more preferably at least four. Yet more preferably, the enzyme has all of the identified proteolytic activities. Preferably, the multifunctional enzyme has substantial anti cell-cell adhesion activity. Preferably, the multifunctional enzyme has substantial homology with the krill multifunctional enzyme.

In one aspect, the present invention provides a method of treating a fungal, bacterial, mycoplasma, parasitic or viral infection by administering a composition comprising the multifunctional enzyme having activity including at least one of a chymotrypsin, trypsin, elastase, collagenase and exo peptidase activity, and a molecular weight between about 20 kd and about 40 kd. Preferred viral targets of treatment include HIV and herpes, particularly genital herpes. Further preferred targets include cold and influenza viruses, preferably treated by pulmonary administration of the enzyme. Other preferred targets include oral, esophageal and vaginal infections, particularly candida infections. Such infections can include topical, pulmonary, urinary tract, intestinal, oral or systemic infections.

In another aspect, the invention provides a method of treating cystic fibrosis (CF) or chronic obstructive pulmonary disease (COPD) patients by administering the multifunctional enzyme of the invention. In another aspect, the invention provides a method of treating the primary and secondary infections of leprosy by administering the multifunctional enzyme of the invention. In another aspect, the invention provides a method of diminishing, removing or preventing corneal scars by applying the multifunctional enzyme of the invention.

In yet another aspect, the invention provides a method of diminishing, removing or preventing dental plaque by applying the multifunctional enzyme of the invention. In still another aspect, the invention provides a method of treating the infections causing certain colitis disease states, certain ulcers and diarrhoea by administering the multifunctional enzyme of the invention. In another aspect, the invention provides a method of treating acne and psoriasis by applying the multifunctional enzyme of the invention. In another aspect, the invention provides a method of treating cancerous tumors by administering orally, intravenously, intraperitoneally, subcutaneously or intra-tumorally a composition comprising the multifunctional enzyme of the invention. In yet another aspect, the invention provides a method of treating blood clots by administering the multifunctional enzyme of the invention. In another aspect, the invention provides a method of treating hemorrhoids by applying to the affected tissue the multifunctional enzyme of the invention.

In still another aspect, the invention provides a method of purifying a multifunctional enzyme to achieve a purity, with respect to macromolecules, of at least about 95%, preferably at least about 99%, more preferably, at least about 99.7%.

In another aspect, the invention provides a purified multifunctional enzyme.

The invention further relates to systemic treatments of autoimmune diseases, such as rheumatoid arthritis, multiple sclerosis and atherosclerosis, and treatments to prevent or reduce immune reactions against transplanted tissue by administering an effective amount of the multifunctional enzyme of the invention. The invention also relates to treating asthma with an effective amount of the multifunctional enzyme of the invention. Preferably, for asthma treatment, the enzyme is administered by the pulmonary route.

The invention also relates to a method of treating a syndrome involving a cell-cell or cell-virus adhesion process comprising administering an anti-adhesion effective amount of a hydrolase reactive with the cellular or viral adhesion acceptor or receptor adhesion molecule that causes the cell-cell or cell-virus adhesion. Preferred treatment targets include inflammation, septic or toxic shock, tumor metastatic processes, an autoimmune diseases, including multiple sclerosis, lupus erythematosus and rheumatoid arthritis, transplantation rejection reactions or microbial infections, including pseudomonas infections of the lungs, HIV infections and herpes infections. The preferred hydrolase for this embodiment is the multifunctional enzyme of the invention.

A preferred embodiment for all of the embodiments described above uses a multifunctional enzyme comprising an N-terminal sequence consisting of I-V-G-G-X-E/D-B-X-X-X-X-Z/B'-P-Z/H-Q-B-X-B'/Z wherein X is any amino acid, Z is an aromatic amino acid, B is an amino acid having a C2 to C6 alkyl side chain, B' is leucine or isoleucine and the remaining single letter designations are standard single letter designations for amino acid residues. Preferably all amino acid residues in the N-terminal sequence are one of the 20 common physiological amino acids. In another preferred embodiment, the first seven N-terminal residues consist of I-V-G-G-X-E/D-B.

In another preferred embodiment, the multifunctional enzyme Thus, in one embodiment, the N-terminal sequence is I-V-G-G-X-E-V-T-P-H-A-Y-P-W-Q-V-G-L-F-I-D-D-M-Y-F (SEQ ID NO:17) shall have at least about 60% homology with the krill derived multifunctional enzyme, more preferably at least about 70% homology, still more preferably at least about 80% homology, yet still more preferably 90% homology. Homology measurements will score conservative substitutions as homologous. "Substantial homology" shall mean at least about 60% homology. The krill multifunctional enzyme is 100% homologous with itself.

Figure 1A:
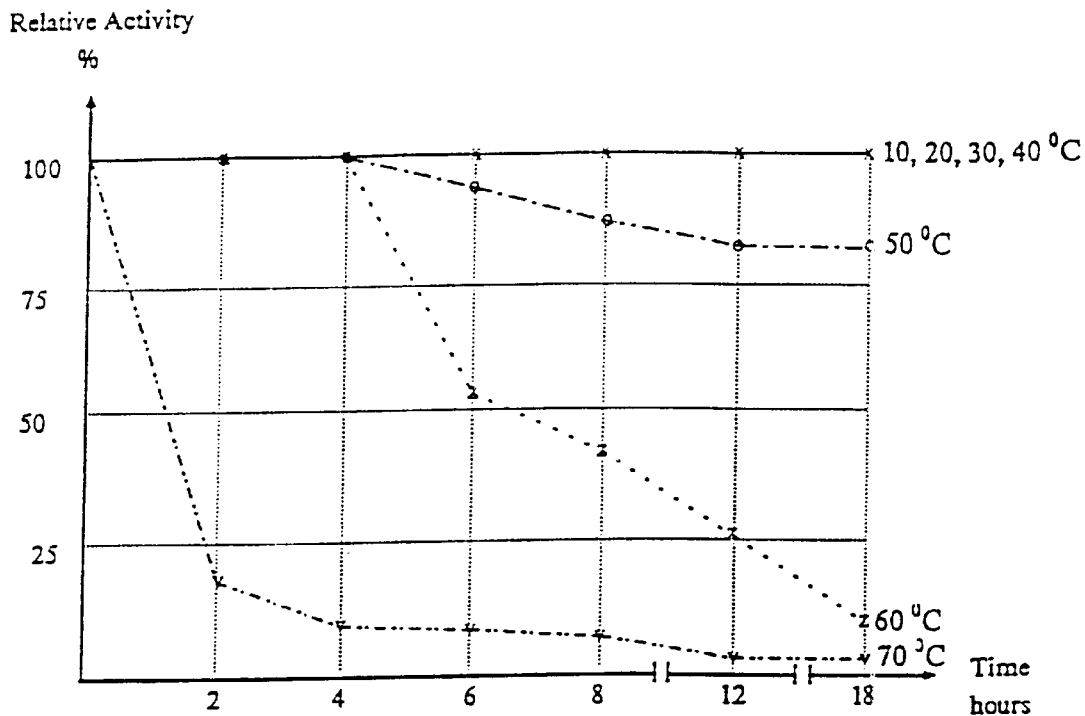
FIGS. 1A and 1B show the temperature stability of partially purified krill multifunctional protease when incubated at various temperatures over time scales of hours or days.
Figure 1B:
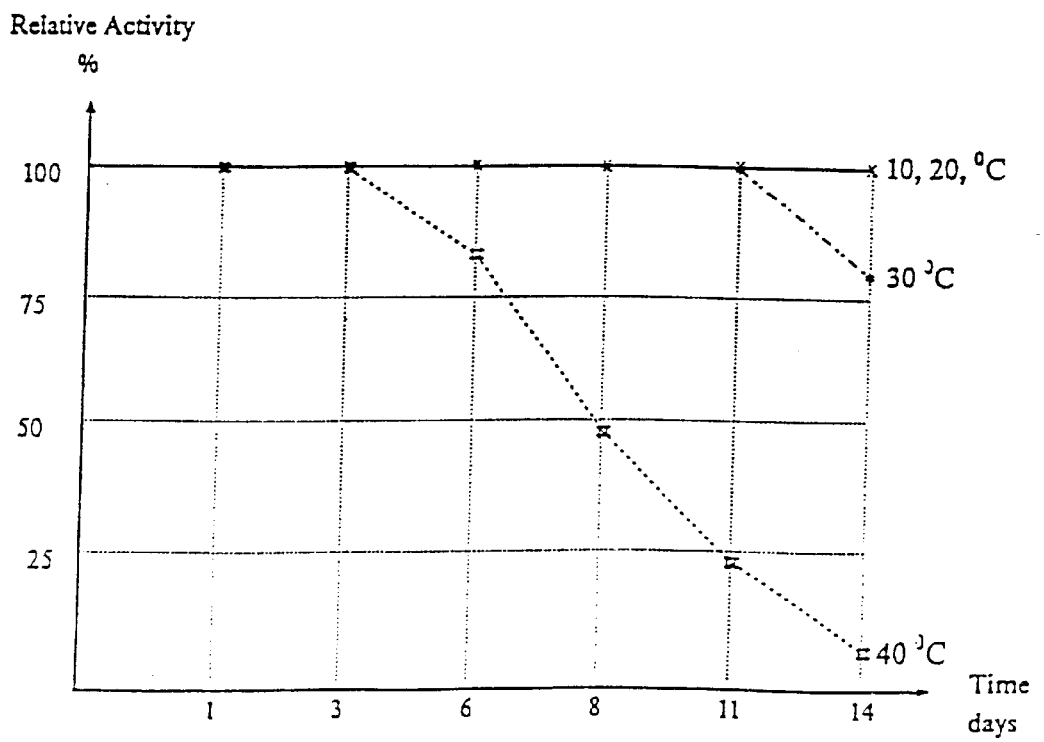

Crustaceans, including antarctic krill, are useful sources for the multifunctional enzyme of the invention. For instance, frozen krill can be homogenized in water or buffer, preferably containing an antimicrobial agent. The supernate, diluted if appropriate, can then be fractionated by ion exchange chromatography (preferably anion exchange chromatography), gel filtration, chromatofocusing chromatography, or other traditional separation process. Preferably, however, some part of the separation process will include affinity chromatography using a matrix having attached molecules of a trypsin inhibitor, such as soybean trypsin inhibitor. The krill enzyme used in the invention can be desorbed from such a matrix by applying conditions that will destabilize the interaction between the enzyme and the inhibitor. Such conditions include high salt, low pH or the presence of denaturants such as urea. To add another selective process, the destabilizing condition will be applied to the matrix incrementally, as in a gradient. When affinity chromatography is used, it will preferably be followed with chromatography using a matrix having attached molecules of the multifunctional enzyme used in the invention. This enzyme affinity step serves to remove molecules of trypsin inhibitor that appear to inevitably leach off the first affinity matrix. By these methods, multifunctional enzyme with a purity in excess of about 95%, even about 99.7%, can be isolated.

The multifunctional enzyme isolated from a non-krill source can be compared to isolated krill multifunctional protease for molecular weight, sequence, temperature or pH stability, temperature or pH optima and proteolytic specificity.

Protease activity can be determined by incubating an enzyme preparation with casein (concentration: 1% w/v) at 30° C. for 20 hours and measuring the release of amino acids or peptides (which can be measured by the increase in colorometrically determinable amino groups). Isolated multifunctional enzyme of 95% purity will typically have a specific activity of at least about 25 Casein Units per mg. (Casein Units are defined in *Biochem. J.*, 173: 291–298, 1978 (using azocasein as the substrate).)

Alternately, tryptic protease activity can be measured against tyrosine-arginine-methyl-ester ("TAME"). The multifunctional enzyme (of at least about 95% purity) will preferably have specific activity of at least about 60 TAME Units per mg. Or, tryptic activity can be measured using Benzoyl-Val-Gly-Arg-p-$NO_2$-anilide as the substrate. Using this substrate and the method of *Biochemical J.*, 185: 423–433, 1980, the multifunctional protease will preferably have specific activity of at least about 210 Units per mg. Chymotryptic activity can be measured using Succinyl-Ala-Ala-Pro-Phe-p-$NO_2$-anilide as the substrate. Using this substrate and the method of *J. Biol. Chem.*, 269: 19565–19572, 1994, the multifunctional enzyme will preferably have specific activity at least about 260 Units per mg. Elastase activity can be measured using Boc-Ala-Ala-Pro-Ala-p-$NO_2$-anilide as the substrate. Using this substrate and the method of *J. Biol. Chem.*, 269: 19565–19572, 1994, the multifunctional enzyme will preferably have specific activity of at least about 270 Units per mg.

Protein purity is generally determined by SDS-PAGE with Coomassive blue staining. The percent staining in the appropriate band reflects he purity. Protein concentrations are generally determined by amino acid analysis or by absorbance at 280 nm.

Generally, the multifunctional enzyme will be sufficiently stabile so that at least about 50% of the proteolytic activity is retained after incubation at 50° C. for 24 hours at pH 7.0 at a concentration of 5 mg/ml. Preferably at least about 50% of the proteolytic activity is retained after incubation at 60° C. for 5 hours at pH 7.0 at a concentration of 5 mg/ml.

Preferably, the pH optimum of the multifunctional enzyme is substrate dependent. For the substrate azocasein, the pH optimum is preferably from about 3.5 to about 6.5, more preferably, from about 4.0 to about 6.0. For the substrate Benzoyl-Val-Gly-Arg-p-nitroanilide, the pH optimum is preferably in excess of about 8.0, more preferably in excess of about 9.0. For the substrate Boc-Ala-Ala-Pro-Ala-p-nitroanilide, the pH optimum is preferably between about 6.0 and about 7.0, more preferably about 7.0.

Using Benzoyl-Val-Gly-Arg-p-nitroanilide as the substrate, the $K_m$ at about pH 9.5 in the presence of 2 mM $Ca^{2+}$ is preferably between about 200 and about 240 $\mu$M. Using Succinyl-Ala-Ala-Pro-Phe-p-nitroanilide as the substrate, the $K_m$ at pH 9.5 in the presence of 2 mM $Ca^{2+}$ is preferably between about 250 and about 290 $\mu$M.

Preferably, the multifunctional enzyme has a temperature optimum for activity against casein of between about 45° C. and about 60° C. Generally, the enzyme retains at least about 50% of its activity when incubated at 5 mg/ml for 18 hours at a pH ranging from about 5.0 to about 9.5 at 25° C.

When HL60 cells are pretreated with the krill multifunctional enzyme, their binding to TNFα stimulated endothelial cells is inhibited by more than about 60%. Preferably, treatment of HL60 or endothelial cells with the multifunctional enzyme of the invention will inhibit HL60 cell binding to TNFα stimulated endothelial cells by at least about 20%, more preferably at least about 40%, still more preferably at least about 60%, yet more preferably at least about 80%. Alternately, the multifunctional enzyme shall preferably have at least about 30% of the adhesion-inhibiting activity of the krill-derived multifunctional enzyme. More preferably, the multifunctional enzyme shall have at least about 60% of the adhesion inhibiting activity of the krill enzyme, still more preferably at least about 80%, yet more preferably at least about 100%.

The multifunctional enzyme of the invention is administered orally, topically, rectally, vaginally, by instillation (for instance into the urinary tract or into fistules), by pulmonary route by use of an aerosol, by application of drops to the eye, or parenterally, i.e. intramuscularly, subcutaneously, intraperitoneallly or intravenously. The multifunctional enzyme is administered alone, or it is combined with a pharmaceutically-acceptable carrier or excipient according to standard pharmaceutical practice. For the oral mode of administration, the multifunctional enzyme is used in the form of tablets, capsules, lozenges, troches, powders, syrups, elixirs, aqueous solutions and suspensions, and the like. In the case of tablets, carriers that is used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the multifunctional enzyme are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol. For topical administrations, the multifunctional protease is typically administered in aqueous form or in a hydrogel. A preferred hydrogel comprises an aqueous suspension of from about 1% (w/v) to about 10% of low molecular weight hydrolyzed starch.

For topical treatments, a suitable dose of multifunctional enzyme per application ranges from about 0.1 $\mu$g/cm$^2$ to about 1 mg/cm$^2$, preferably from about 10 $\mu$g/cm$^2$ to about 250 $\mu$g/cm$^2$. For systemic treatments, dosages will generally be selected to maintain a serum level of multifunctional protease between about 0.1 $\mu$g/100 cc and about 5 $\mu$g/100 cc, preferably between about 0.5 $\mu$g/100 cc and about 2.0 $\mu$g/100 cc. For ocular treatments, a suitable dose of multifunctional enzyme per application ranges from about 0.01 mg per eye to about 5 mg per eye, preferably from about 0.1 mg per eye to about 2.0 mg per eye. For vaginal and urinary tract treatments, suitable flushing/instillation solutions of the multifunctional enzyme will generally have concentrations from about 1 mg/ml to about 15 mg/ml, preferably from about 3 mg/ml to about 6 mg/ml. For oral treatments, suitable mouthwash solutions will generally have concentration of multifunctional enzyme from about 1 mg/ml to about 15 mg/ml preferably from about 2 mg/ml to about 10 mg/ml. Aerosols will generally be made from solutions having enzyme concentrations from about 0.1 mg/ml to about 15 mg/ml, preferably from about 1 mg/ml to about 10 mg/ml. For all treatments, the enzyme composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect.

For wound healing, the multifunctional enzyme shall preferably be applied more often than simply the time at which the wound is first dressed. Preferably, the multifunctional enzyme shall be applied at least about every time the wound dressing is changed. Alternately, the multifunctional enzyme will be applied at least about every other day, more preferably, every day.

For organ transplants, the organ to be transplanted will preferably be bathed in a solution of the multifunctional enzyme for between about 10 minutes and about 5 hours. The enzyme solution will preferably contain between about 0.1 mg/ml and about 25 mg/ml of the multifunctional enzyme, more preferably, between about 0.5 mg/ml and about 5 mg/ml. After transplantation, the multifunctional enzyme will preferably be administered systemically using the conditions described above.

For leprosy, many of the associated infections will be appropriately treated with a topical application of the multifunctional enzyme. For CF or COPD, the multifunctional enzyme can be used to treat (a) the build up of viscous fluids in the lungs and (b) associated pulmonary infections.

Preferably, treatments of CF and COPD patients shall include treatments with an aerosol of the multifunctional enzyme, but can include systemic administrations.

For adhesion disorders, the cells or viruses involved can include, without limitation, endothelial cells, lymphocytes, including T-cells, tumor cells, microbial cells, viruses, including HIV and herpes. Adhesion processes are believed to be involved in tissue invasion, for instance, by immune cells, microbes, and tumor cells.

"Hydrolases," as used in conjunction with the anti-adhesion embodiment of the invention relates to enzymes that degrade bonds formed by dehydration reactions such as amide, ester, or ether bonds. Preferred hydrolases are proteases. Particularly preferred is the multifunctional enzyme of the invention. "Reactive" with a cellular or viral acceptor or receptor adhesion molecule shall mean reactive to disable the molecule's ability to interact with the corresponding acceptor or receptor adhesion molecule.

Generally, the multifunctional enzyme will be administered in an effective amount. An effective amount is an amount effective to either (1) reduce the symptoms of the disease sought to be treated or (2) induce a pharmacological change relevant to treating the disease sought to be treated. For cancer, an effective amount shall further include an amount effective to: reduce the level of metastasis; reduce the size of a tumor; slow the growth of a tumor; and increase the life expectancy of the affected animal. For wound treatment, in one aspect, an effective amount shall include an amount which, if regularly applied, prevent the occurrence of infection. In another aspect, for wound healing, an effective amount includes an amount effective to reduce the average time it takes for a wound to heal.

Humans are the preferred subjects for treatment. However, the multifunctional enzyme can be used in many veterinary contexts, as will be recognized by those of ordinary skill in light of the present disclosure. For the purposes of this application, "microbes" shall encompass bacteria, mycoplasma, yeast or fungi, viruses and parasites (such as malaria parasites).

The krill derived multifunctional enzyme has been observed to treat infections. However, its direct effect on the growth of microbes in vitro is small. While not wishing to be limited by theory, it is believed that the enzyme attacks the mechanisms by which microbes and tumors invade tissues. These mechanisms include cell-cell adhesion mechanisms by which a tumor or microbe may establish itself in a tissue. The disruption of other cell-cell adhesion reactions by the multifunctional enzyme is believed to be relevant to other conditions that are treatable with the multifunctional enzyme, including dental plaque and immune disorders.

As used herein, "immune disorders" means any disorder caused by an immune reaction to autologous or transplanted tissue.

As demonstrated in parent U.S. application Ser. No. 08/338,501, preparations of the multifunctional enzyme are active even when not purified to homogeneity. In an illustrative purification, frozen krill is thawed and homogenized. An equal volume of distilled water containing 0.02% (w/v) sodium azide is added, and the admixture stirred for about 6 hours at about 4° C. Then, the supernate is collected by centrifugation. The supernate is defatted by adding ethyl acetate and stirring overnight at 4° C. The fat-containing ethyl acetate layer can then decanted and the aqueous extract evaporated sufficiently to remove the ethyl acetate. Ammonium sulfate is added to the extract to about 60% saturation at about 4° C. and the mixture stirred overnight. The salted out precipitate is isolated by centrifugation. The precipitate is dissolved in phosphate buffered saline ("PBS", 0.05 M sodium phosphate, pH 7.4, 0.05 M sodium chloride) and dialyzed (using a 10 kd molecular weight cutoff) against PBS.

The redissolved precipitate is applied to a cross-linked agarose gel filtration column (Sephacryl 200, Pharmacia, Sweden) and the fractions displaying absorbance at about 280 nm are assayed for proteolytic activity. The combined proteolytically active fractions are pooled and lyophilized. A "poly-enzyme" preparation containing about six bands with apparent molecular weights (by SDS PAGE) ranging from about 24 to 34 kd can be isolated from-antarctic krill in this way.

At least one of the enzymes present in the poly-enzyme preparation is multifunctional and has at least one of chymotrypsin, trypsin, elastase, collagenase and exo peptidase activity. This enzyme can be substantially purified by traditional methods to an apparent purity of about 90%. The krill-derived multifunctional enzyme displays an apparent molecular weight of about 29 kd.

Useful preparations of poly-enzyme preparation will generally comprise, with respect to proteins, at least about 10% of the multifunctional enzyme. Preferably preparations of poly-enzyme preparation will comprise at least 30% of the multifunctional enzyme.

Figure 2:
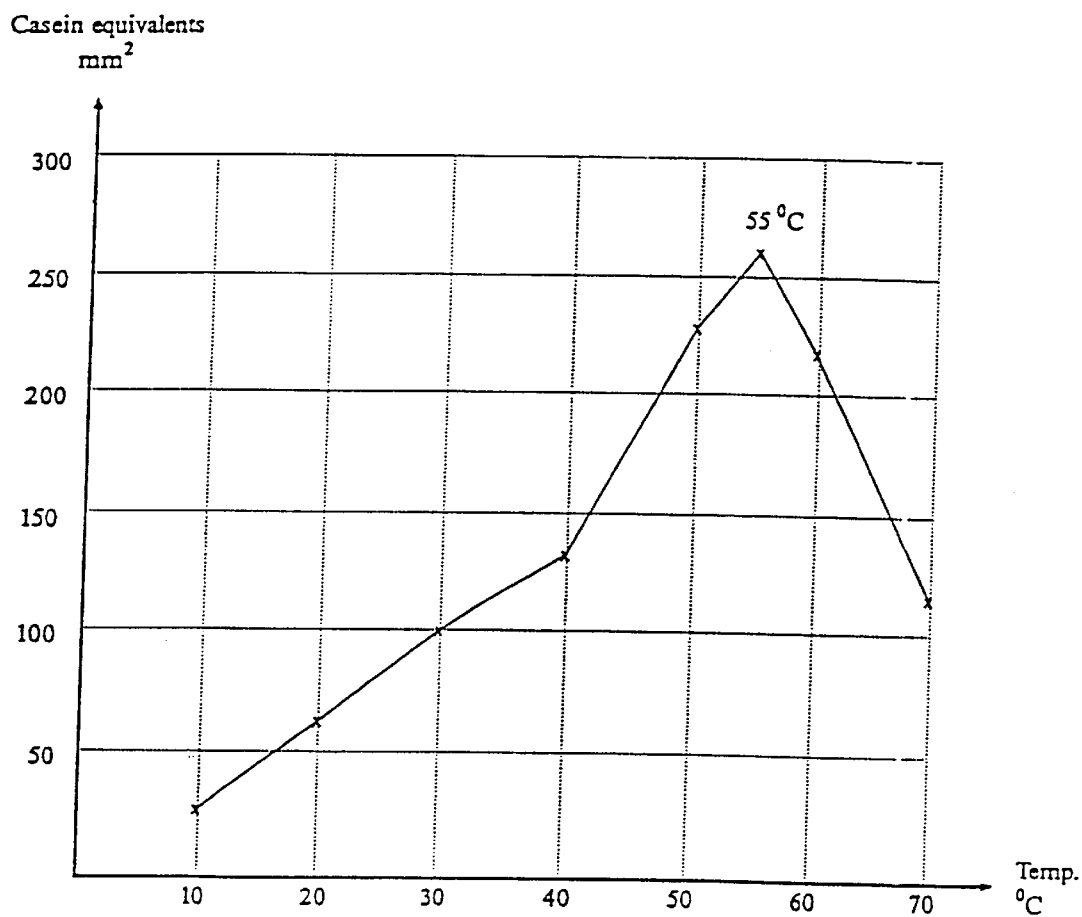
FIG. 2 shows the temperature optimum of partially purified krill multifunctional enzyme.
Figure 3:
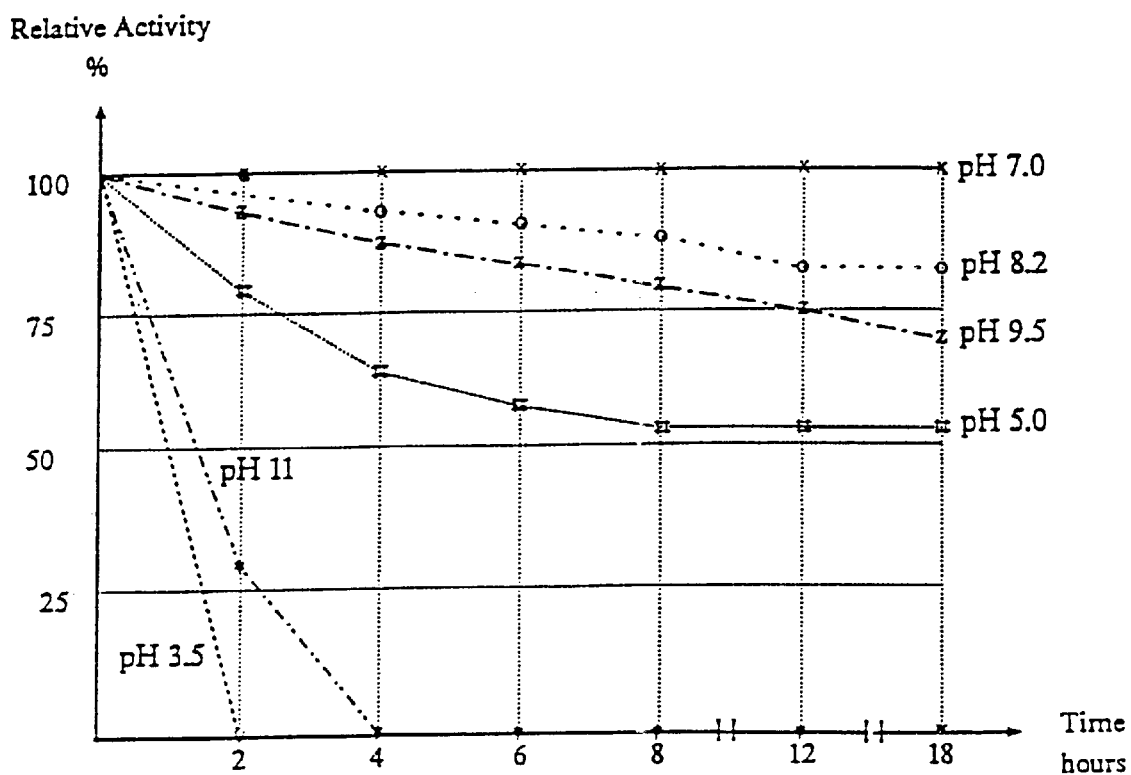
FIG. 3 shows the pH stability of partially purified krill multifunctional enzyme.

In FIG. 1A and B, the temperature stability profiles the krill poly-enzyme preparation are displayed. Preparations of enzyme (5 mg/ml, buffered at pH 7.0) were incubated at 10, 20, 30, 40, 50, 60 or 70° C. for various times and subsequently assayed for the ability to release amino acids and peptides from bovine casein (available from Bio-Rad Laboratories, Inc., Hercules, Calif.) after 20 hours incubation at pH 7.0. At 60° C., the preparation has a half-life in excess of 6 h; at 50° C., the half-life is well in excess of 24 h; and, at 40° C., the half-life is about 6 days. FIG. 2 displays a profile of the activity of the poly-enzyme preparation at various temperatures. The temperature optimum is 55° C. FIG. 3 displays a profile of the activity of the poly-enzyme preparation after incubation at room temperature at various pH values. Following the incubation, the pH was adjusted to about pH about 7.0, and the remaining activity determined as described above. The optimum stability is achieved at about pH 7.0. However, at least 50% of the original activity is retained following about 18 h incubations in solutions having pH values between about 5.0 and about 9.5.

The multifunctional enzyme can be purified from tissue homogenates of fish or crustaceans or from homogenates or supernates derived from a cell culture of transformed or normal prokaryotic or eukaryotic cells that produce the multifunctional enzyme. The preferred purification comprises the use of an affinity column comprising an inhibitor reactive with the multifunctional protease. After the enzyme is eluted from the affinity column, residual enzyme inhibitor in the preparation is removed. One method of doing this is to pass the preparation over an affinity matrix comprising a molecule, typically a protease, with which the inhibitor binds strongly (for instance, with an affinity constant of at least about $10^6$ M, preferably at most about $10^7$ M). More preferably, the affinity legend is a previously isolated preparation of the multifunctional enzyme that the procedure seeks to purify.

Some amount of traditional protein purification will preferably be done prior to the affinity chromatography step. This can include differential precipitation, gel filtration chromatography, ion-exchange chromatography, chromatography on weakly hydrophobic matrices such as dye matrices, chromatofocusing and reversed phase liquid chromatography. Preferably, these one or more steps will be sufficient to remove all proteins, other than the multifunctional protease, that bind to the affinity ligand. Alternately or supplementally, one or more traditional protein purification steps can be applied after the affinity chromatography step.

A preferred purification comprises the steps of:
1) providing a supernate of a homogenate of an appropriate biological source;
2) applying the supernate to a anion exchange column;
3) washing the column with a buffer of an aqueous solution of selected ionic strength $I_1$;
4) eluting the column with an aqueous solution of selected ionic strength $I_2$; and
5) collecting the eluted solution comprising the multifunctional enzyme, wherein $I_1$ is selected to be sufficient to (1) elute all proteins that bind a selected protease inhibitor reactive with the multifunctional enzyme, but bind to the anion exchange column more weakly than the multifunctional enzyme and (2) not elute the multifunctional enzyme, and wherein $I_2$ is greater than $I_1$ and is selected to elute, among proteins that bind the selected protease inhibitor only the multifunctional enzyme.

The method also further comprises the steps of, after step 5:
6) applying the eluted solution to an affinity matrix comprising the protease inhibitor reactive with the multifunctional enzyme;
7) eluting the affinity matrix with an aqueous solution that destabilizes the interaction between the multifunctional enzyme and the protease inhibitor; and
8) collecting a second eluted solution comprising the multifunctional enzyme.

These preferred methods surprisingly yield, after a few steps, homogeneous preparations of multifunctional enzyme.

The method further comprises the steps of, after step 8:
9) applying the second eluted solution to an affinity matrix having a prior preparation of the multifunctional enzyme; and
10) collecting the effluent from the enzyme-containing affinity matrix, the effluent comprising the purified multifunctional enzyme.

Preferably, $I_1$ is about the ionic strength of 0.4M NaCl and $I_2$ is about the ionic strength of 0.6 M NaCl. Preferably, the anion exchange chromatography is conducted at a pH between about 5.5 and about 7.5, more preferably between about 6.0 and about 7.0, yet more preferably about 6.2. Preferably, the anion exchange matrix comprises a polysaccharide-based matrix comprising, in the swelled state, between about 0.05 mmol and about 0.6 mmol anion exchange sites per ml. Preferably, the matrix is a cross-linked dextran of the type sold under the tradename Sepharose. Preferably, the anion exchange groups comprise diethylaminoethyl (DEAE) or quaternaryaminoethyl (QAE) groups, more preferably DEAE groups.

The affinity chromatography of steps 6–8 preferably further comprise, between steps 6 and 7, washing the inhibitor-containing column with a solution having ionic strength of at least about that of 0.5 M NaCl, more preferably of about 0.8 M NaCl, yet more preferably of about 1M NaCl. This step and the prior eluting step will preferably be conducted at a pH between about 5.5 and about 7.5, preferably between about 6.0 and about 7.0. The eluting step 7 preferably comprises applying a buffer having pH of about 2 to about 4, preferably about 3. Alternately, it may preferably comprise applying a buffer having pH of at least about 8. The eluting buffer will preferably have sufficient ionic strength to suppress weak ionic interactions with the affinity matrix.

Steps 9 and 10 of the method will preferably be conducted at a pH between about 5.5 and about 7.5, more preferably between about 6.0 and about 7.0. The buffer used in these steps will preferably have sufficient ionic strength to suppress weak ionic interactions with the affinity matrix.

The matrix used to create the affinity matrices will preferably comprise a carbohydrate matrix such as cross-linked dextran (e.g. that sold under the tradename Sepharose) or agarose (e.g., that sold by Pharmacia, Sweden as "Sephacryl"). The matrix should have pore sizes sufficient to admit both the affinity ligand that will be attached to the matrix and the multifunctional enzyme of the invention. Methods of synthesizing appropriate affinity columns are well known. See, for instance, Axén et al., *Nature*, 214:1302–1304, 1967.

It will be apparent to those of ordinary skill that the enzyme can be manufactured by recombinate means. For instance, the sequences recited herein can be used as the basis of oligonucleotide probes for screening expression or genomic libraries to isolate the complete structural gene. See, e.g., Suggs et al., *Proc. Natl. Acad. Sci. USA*, 78: 6613, 1981 or Berent et al., *BioTechniques*, 3: 208, 1985. Alternately, these sequences can be used as the basis for a PCR-based gene amplification method. See generally, *Molecular Cloning: A Laboratory Manual, second edition*, Cold Spring Harbor, 1989 and *PCR Protocols, A Guide to Methods and Applications*, edited by Michael et al., Academic Press, 1990. Once fully identified, these structural genes can be edited and appropriately inserted into expression vectors by methods known to the art.

These structural genes can be altered by mutagenesis methods such as that described by Adelman et al., *DNA*, 2: 183, 1983 or through the use of synthetic nucleic acid strands. The products of mutant genes can be readily tested for multifunctional enzymic activity.

The invention is exemplified with the following nonlimiting examples. The examples may refer to the "multifunctional enzyme", in which case a preparation of at least about 90% purity was used, or they may refer to a "poly-enzyme" preparation, described above, which is a heterogeneous preparation containing the multifunctional enzyme.

EXAMPLE 1

Protease Activity

The multifunctional enzyme can be compared to isolated krill multifunctional protease for molecular weight, sequence, temperature or pH stability, temperature or pH optima and proteolytic specificity.

EXAMPLE 1A

Specificity

To study proteolytic specificity, the following substrates are used:

| Substrate | Type of Activity |
|---|---|
| Succinyl-Ala-Ala-Pro-Phe-pNO$_2$ anilide | Chymotrypsin |
| Boc-Ala-Ala-Pro-Ala-pNO$_2$ anilide | Elastase |
| Benzoyl-Val-Gly-Arg-pNO$_2$ anilide | Trypsin. |

These substrates are used to measure the proteolytic activities of the multifunctional enzyme. These studies include measurements of $K_m$ and $K_{cat}$.

EXAMPLE 1B
Exo Peptidase Activity

Multifunctional enzyme from Krill (1 mg) was dissolved in 5 ml buffer together with 1% (wt/v) bovine casein and incubated at 20° C. for 24 hours. The buffer was 0.1M sodium phosphate, pH 7.5. After 24 hours, 10% trichloroacetic acid was added to precipate the proteins present in the solution. The supernate was collected and reacted with ninhydrin. The ninhydrin was used from a 2% solution in 3:1 DMSO: 4M Lithium Acetate, pH 5.2, as instructed by the supplier, Sigma Chemical, Co., St. Louis. The reacted supernate was applied to a cross-linked acrylamide column (Biorad P-2, Bio-Rad, Hercules, Calif.) to separate reacted amino acids from reacted peptides. The concentration of amino acids in the amino acid fraction was determined from the absorbance at 820 nm. A 1% solution of undigested casein was treated in the same way as a control. The control had an absorbance of less than 0.01, while the amino acid fraction of the digest displays an absorbance of 0.28 (at equivalent dilutions).

EXAMPLE 1C
pH Optima

The candidate multifunctional enzymes are tested for proteolytic activity against various substrates in solutions having various pH values, such as pH values between 4 and 10, to determine the pH optima against a given substrate. These optima can be compared to the corresponding optima for the krill multifunctional enzyme.

EXAMPLE 1D
Protease Inhibitors

The effectiveness of various protease inhibitors is used to examine the relatedness of the various candidate multifunctional enzymes. These inhibitors include $\alpha_1$- protease inhibitor, $\alpha_1$-antichymotrypsin, anti-thrombin III, $\alpha_2$-macroglobin, bovine pancreas protein inhibitor, and soybean protein inhibitor. These inhibitors are available from Sigma Chemical Co, St. Louis, Mo. $K_i$ values are determined in solutions of various pHs using a number of protease substrates, including TAME, Benzoyl-Val-Gly-Arg-p-$NO_2$-anilide, Succinyl-Ala-Ala-Pro-Phe-p-$NO_2$-anilide, Boc-Ala-Ala-Pro-Ala--p-$NO_2$-anilide and azocasein.

EXAMPLE 2
In Vitro Binding of HL60 Cells to Endothelial Cells

HL60 cells (a human lymphocyte cell line, available from the European Cell Culture Bank under ECACC Accession No. 85011431) adhere to human endothelial cells. The endothelial cells used in the experiment are described in Edgell et al., *Proc. Natl. Acad. Sci. USA* (1983) 80:3734. The HL60 cells are described in *Blood* (1979) 53:713 and *Nature* (1977) 270:347. Their adhesion to endothelial cells is believed to model a mechanism for tumor cell invasion and infection more generally. This adhesion is stimulated by tumor necrosis factor $\alpha$ ("TNF$\alpha$") and inhibited by antibodies to the E-selectin antigen on HL60 cells. E-selectin is a cell surface adhesion protein that appears to bind to a sialated carbohydrate. See, Bevilacqua et al., *Science* (1989) 243:1160.

To measure the above described effects, endothelial cells were first passaged onto 96 well plates at a given concentration. The cells were incubated at 37° C. under a DMEM cell culture medium containing 10% fetal calf serum and under a 5% $CO_2$ atmosphere. Then, the medium was removed and replaced with 100 µl of a suspension of 200,000 HL60 cells in RPMI medium containing 10% fetal calf serum. The cells were incubated for 30 minutes. After this, the medium was removed and the adherent cells were washed two times with DMEM medium. The relative adherence of the HL60 cells was measured by measuring the difference in optical density at 450 nm between the plates on which the cells were co-incubated and plates having endothelial cells alone.

The effect of TNF$\alpha$ was measured by adding TNF$\alpha$ at 1500 units/ml to the endothelial cells 4 hours before the incubation with HL60 cells. The effect of antibody to E-selectin was measured by adding 25 µg/ml of monoclonal antibody BBAZ (R&D Systems Europe, Oxford, England) to the HL60 cells. The results of the experiments outlined above were:

| Expt. No. | HL60 Cells | Endothelial Cells | Absorbance* |
|---|---|---|---|
| 1 | no treatment | no treatment | 0.324 |
| 2 | no treatment | pretreated with TNF$\alpha$ | 0.444 |
| 3 | added in the presence of mAb to E-selectin | pretreated with TNF$\alpha$ | 0.357 |

*increase over absorbance of endothelial cells alone

The effects of the isolated, krill multifunctional protease on this system were measured by:

(1) measuring the effect of adding to the endothelial cells 92.3 µg/ml isolated, krill multifunctional enzyme together with the HL60 cells;

(2) After pretreating the endothelial cells with TNF$\alpha$ for 2 hours, adding 92.3 µg/ml isolated, krill multifunctional enzyme and incubating for 2 more hours prior to the addition of HL60 cells; or (3) Pretreating the HL60 cells with 92.3 µg/ml isolated, krill multifunctional enzyme prior to adding the HL60 cells to the plates of endothelial cells.

The results of these experiments were as follows:

| Expt. No. | HL60 Cells | Endoth Cells | Absorbance* |
|---|---|---|---|
| 4 | Multifunctional enzyme added simultaneously with cells | pretreated with TNF$\alpha$ | 0.425 |
| 5 | no treatment | Four hours pretreatment: 0–4 h TNF$\alpha$ 2–4 h multifunctional enzyme | 0.247 |
| 6 | pretreated with multitunctional enzyme for 2 h | pretreated with TNF$\alpha$ | 0.160 |
| 7 | pretreated with multifunctional enzyme for 2 h | Four hours pretreatment: 0–4 h TNF$\alpha$ 2–4 h multifunctional enzyme | 0.059 |

*increase over absorbance of endothelial cells alone.

To confirm these results, the number of adhering HL60 cells were counted by removing them from the plate and counting the cells. The number of HL60 cells was determined by subtracting the cell numbers for control plates having only endothelial cells. These counting results mirrored the optical density results, as follows:

| EXPERIMENT | HL60 CELL NUMBER |
|---|---|
| 1 | 32,590 |
| 2 | 43,990 |
| 3 | 35,730 |
| 4 | 42,190 |
| 5 | 25,280 |
| 6 | 17,010 |

These adherence studies show that isolated, krill enzyme destroyed the cell-surface ligand and acceptor molecules that facilitate cell-adhesion. The function of other multifunctional proteases can be examined by the same method.

EXAMPLE 3
Cell Binding Comparisons

The effectiveness of various members of the multifunctional enzyme family, i.e., the non-krill multifunctional enzymes having at least about 60% homology with the krill enzyme, are compared with that derived from krill using the HL60 binding assay of Example 2.

Figure 4:
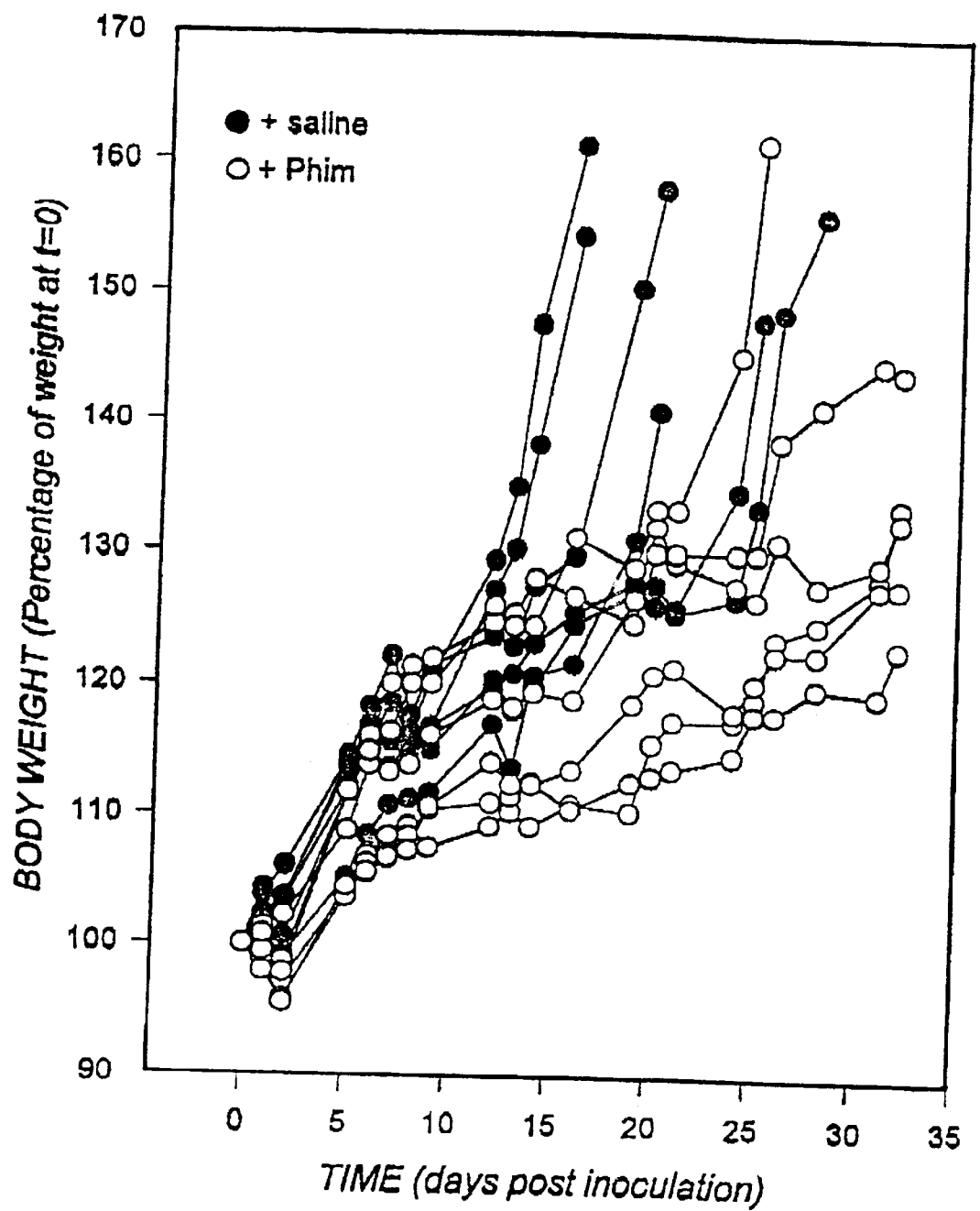
FIG. 4 shows the weight gain of enzyme treated or untreated mice having a soft ovarian-derived tumor.
Figure 5:
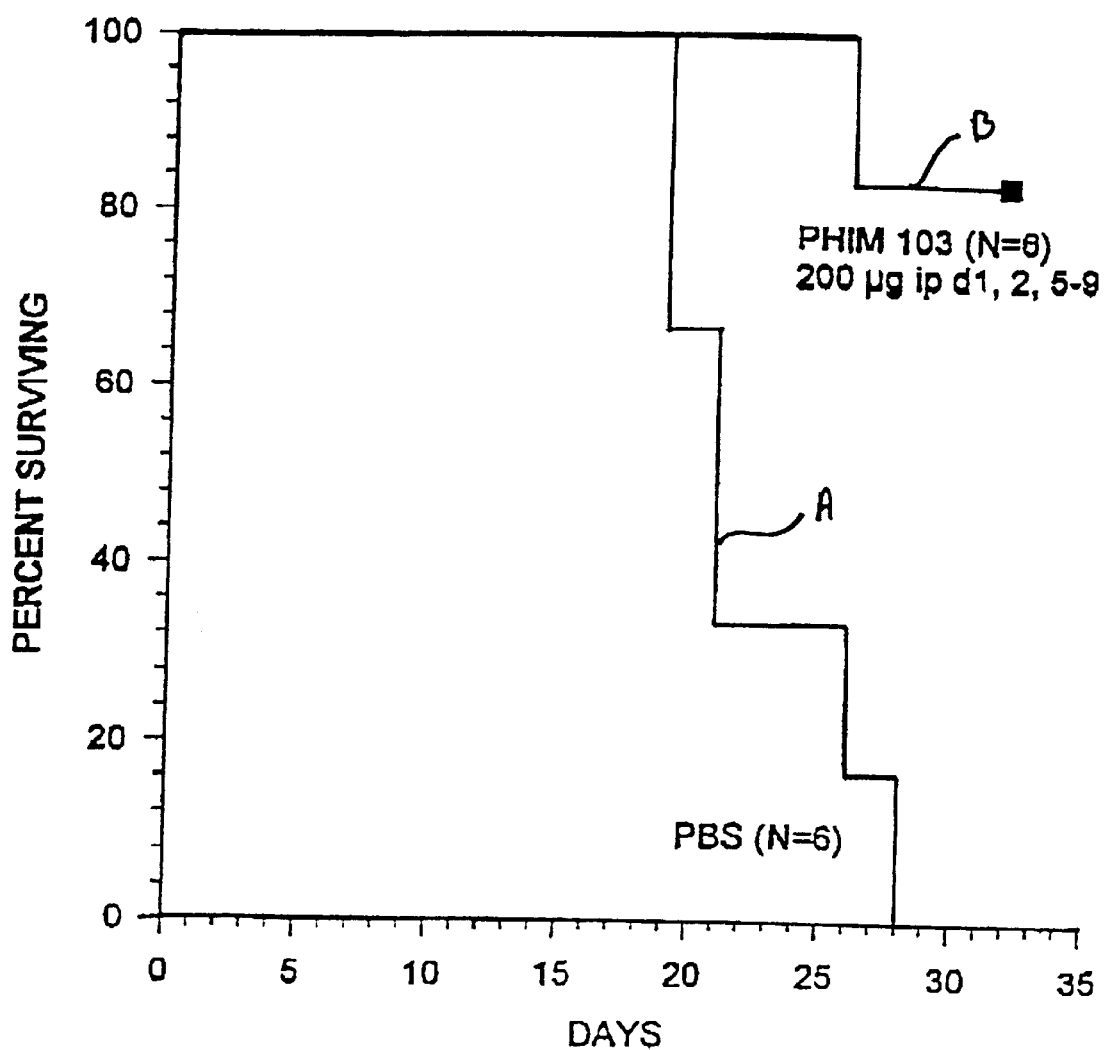
FIG. 5 shows the survival of enzyme treated and untreated mice containing the ovarian tumor.

EXAMPLE 4
Mouse Ovarian Tumor Treatment 25,000 mouse ovarian tumor cells were injected into the abdominal cavity of 12 mice. On days 1, 2 and each of days 5–9, either saline or 200 μg of krill multifunctional enzyme dissolved in 1 ml saline was injected into the ascites. In FIG. 4, weight gains (an indication of tumor growth) for saline treated (dark circles) and enzyme treated (open circles) mice are shown. In FIG. 3, the percentage of the animals surviving over time for saline (line A) and enzyme (line B) treated mice.

EXAMPLES 5–6

Examples 5–6 addressed the safety of krill multifunctional enzyme preparations.
Example 5—Toxicology Separate groups of male and female rats (Crl:CD(SD) BR strain, Charles River Ltd, Margate, UK; 5 rats per group) were treated by the I.V. route with 0, 0.5, 5 and 50 mg/kg per day over 7 days. After seven days, these dosages resulted in small decreases in hemoglobin ("Hb"), red blood cell count ("RBC") and packed cell volume ("PCV"), as shown in the table below:

| Group | Dose | Sex | HB | RBC | PCV | MCV* | MCH* | MCHC* |
|---|---|---|---|---|---|---|---|---|
| 1 | 0 | M | 14.8 | 6.79 | 44.3 | 65.4 | 21.8 | 33.4 |
|   |   | F | 14.7 | 6.76 | 43.7 | 64.6 | 21.7 | 33.6 |
| 2 | 0.5 | M | 14.0 | 6.35 | 41.8 | 65.9 | 22.2 | 33.6 |
|   |   | F | 13.8 | 6.12 | 40.5 | 66.3 | 22.5 | 33.9 |
| 3 | 5 | M | 13.8 | 6.25 | 41.1 | 65.8 | 22.1 | 33.6 |
|   |   | F | 13.4 | 5.94 | 39.9 | 67.2 | 22.6 | 33.6 |
| 4 | 50 | M | 13.1 | 6.19 | 39.1 | 63.3 | 21.3 | 33.6 |
|   |   | F | 13.0 | 6.01 | 38.8 | 64.6 | 21.7 | 33.6 |

*MCV = mean corpuscular volume
MCH = mean corpuscular hemoglobin
MCHC = mean corpuscular hemoglobin concentration None of the treated animals showed any visible symptoms of illness or adverse reaction. The same experiments are done with other multifunctional proteases.
Example 6—Toxicity on Mice The toxicity of poly-enzyme preparation has also been tested on mice with s.c. implanted P388 murine leukemia (a chemically induced cancer) and compared with doxorubicin, a well known anti-cancer drug (abbreviation DOX). The results are summarized in the following Table. No mouse treated with poly-enzyme preparation or in the control group died or lost weight, whereas all mice in the doxorubicin group, except for those receiving the lowest dosage, lost weight and died. The highest dose of poly-enzyme preparation (20 mg/kg) is far higher than any of the doses used in the clinical examples described below.

Toxicity of poly-enzyme preparation and DOX administered i.p. daily during 9 consecutive days to mice with P388 murine leukemia

| Drug weight (g) | Dose (mg/kg) | Toxic death | Body change |
|---|---|---|---|
| Control | 0 | 0/6 | +2.3 |
| Krill | 20 | 0/6 | +3.3 |
| poly-enzyme | 10 | 0/6 | +3.3 |
| preparation | 5 | 0/6 | +3.3 |
| DOX | 5 | 6/6 | −2.3 |
|  | 2.5 | 6/6 | −0.6 |
|  | 1.25 | 0/6 | +0.5 |

The same experiments are done with other multifunctional proteases.

EXAMPLES 7–35

Examples 7–35 examine the effectiveness of krill multifunctional enzyme in treating a number of disease states.
Example 7—Infections in Post-Operative Surgical Wounds Forty patients were included in this study and they were divided into two groups of 20 patients each, representing 41 post-op. abdominal (34) and thoracic (7) wounds. Preparations of isolated, krill multifunctional enzyme (3 Casein-Units/ml), and krill poly-enzyme preparation (5 Casein-units/ml) were tested in each group. Prior to use, the enzymes were stored as lyophilized white powders without preservatives or anti-microbial additives. The preparations were reconstituted in saline prior to use.

The patients had an average age of 52±16 years, and included 28 males and 12 females. Enzyme preparations were applied to the wounds 2 times daily in an amount of 25 mg/treatment. Within 5 days all infections were brought to a subclinical level and all apparent signs of clinical infections were gone. No notable difference between the two preparations could be observed. There were no apparent adverse reactions.
Example 8—Infected Wound A 3 month old boy who had been operated on for a hydro cele och scrotal hernia developed by 10 days after surgery a serious infection at the site of the incision. The infected incision exuded pus. Parts of the incision threatened to split open after the stitches were removed. The boy was treated twice daily for 3 days with dressings which had been soaked in the poly-enzyme preparation (4 mg per treatment). After 3 days of treatment the infection was gone and the wound had healed.

Example 9—Scleroderma

The patient suffered from chronic hardening and thickening of the skin, i.e., scleroderma in his fingertips on his right hand. He was treated by twice daily applying 0.5 ml of hydrogel containing 0.5 mg/ml of the krill multifunctional enzyme. The pain associated with the condition was substantially reduced within 48 hours, and after three weeks all cracks were healed. Treatment was discontinued after three weeks. No recurrence occurred during six weeks of follow up.

Example 10—Prophylactic Treatment of Post-Surgical Wounds

Isolated, krill multifunctional enzyme (1) and krill poly-enzyme preparation (2) were tested against a sterile 0.9% NaCl control solution, (3) as a prophylactic anti-microbial rinsing solution on post-op. wounds. Each of the three treatment groups included 20 patients.

Non-bleeding post-op. wounds were treated twice daily with saline, isolated multifunctional enzyme solution (3 Casein Units/ml) or poly-enzyme preparation (5 Casein Units/ml). The wounds were rinsed thoroughly with the respective solution and covered with sterile gauze under a semi occlusive dressing. At each redressing, the wounds were inspected for infection, inflammation, erythema, swelling, heat, necrotic tissue, fibrin, pus, bleeding, pain and possible adverse reactions.

No post-op. clinical infections occurred in the groups treated with isolated enzyme or multi-enzyme solutions nor was acute inflammation or erythema observed in any of the patients in these two groups. For both groups treated with protease, 18 wounds were healed (>90% epithelialization) within 10 days treatment. No adverse reactions were observed. In the control group 4 patients developed severe invasive infections and additional 2 patients developed acute inflammations. Erythema, swelling and pain were frequent observations in this group. 14 wounds were healed within 10 days of treatment.

Example 11—Small Size Burns

Eleven patients with small, full thickness burns infected by *S. aureus* and *P. aeruginosa* and who did not respond to antibiotics and silverdiazine cream were included in this study. 5 patients were treated with isolated, krill multifunctional enzyme in a hydrocolloid cream (3 Casein-Units/ml) and 6 patients with the krill poly-enzyme preparation in solution (5 Casein-Units/ml). The multi-enzyme preparation was reconstituted in saline prior to use. The isolated multi-functional enzyme was mixed with hydrocolloid gel an aqueous gel containing 0.8% w/v Carbopol™ (Dow Corning, Midland, Mich.) and 23.5% w/v glycerin prior to use. (Carbopol™ is a vinyl polymer with active carboxy groups described in *Chem. Eng. News* 36:64 (1958).)

Wounds were treated two times daily with 25 mg/treatment of multifunctional enzyme. All wounds were completely free from all signs of infection within 5 days treatment. The lack of infection was confirmed by MO-cultivation. Necrotic tissue, pus and fibrinous fibrils in the granulation tissue were effectively decomposed by both preparations and no perceptible difference in efficacy between the preparations could be observed. No adverse reactions were observed.

The test results are summarized in Table 1.

| Wound No./ Size (cm$^2$) | Strain | MO-status before (10$^3$) | Visual Percentage of |||||  Preparation | Day of termin. | MO-status after (10$^3$) | Visual percentage of ||||| Healed post-treatm. |
|---|---|---|---|---|---|---|---|---|---|---|---|---|---|---|---|---|
| | | | Necr. | Pus | F/brin | Gra-nul. | Epith. | | | | Necr. | Pus | F/brin | Granu. | Epith. | |
| I 1.5 | P. aerig. | 16 | 20 | 60 | 20 | | | Solution | 3.5 | <1 | | | | 30 | 70 | 3 |
| II 4.0 | P. aerig. | 18 | 50 | 10 | 40 | | | Gel | 5.0 | <1 | | | 10 | 60 | 30 | 11 |
| III 3.6 | S. aureus | 22 | 10 | 90 | | | | Gel | 3.0 | <1 | | | 10 | 40 | 50 | 6 |
| IV 2.4 | P. aerig. | 14 | 40 | 10 | 50 | | | Gel | 3.0 | <1 | | | | 50 | 50 | — |
| V 2.8 | S. aureus | 17 | | 100 | | | | Solution | 4.0 | <1 | | | | 30 | 70 | 7 |
| VI 1.9 | S. aureus | 16 | | 100 | | | | Solution | 2.5 | <1 | | | | 20 | 80 | 4 |
| VII 4.5 | S. aureus | 15 | 10 | 80 | 10 | | | Gel | 5.0 | <1 | | | 10 | 60 | 30 | 15 |
| VIII 3.2 | P. aerig. | 12 | 40 | 40 | 20 | | | Solution | 3.0 | <1 | | | | 60 | 40 | 6 |
| IX 1.8 | S. aureus | 16 | 10 | 90 | | | | Solution | 2.5 | <1 | | | | 20 | 80 | — |
| X 1.3 | P. aerig. | 17 | 30 | 30 | 40 | | | Gel | 3.5 | <1 | | | | 40 | 60 | 8 |
| XI 3.1 | P. aerig. | 20 | 30 | 30 | 40 | | | Solution | 5.0 | <1 | | | 10 | 80 | 10 | 18 |

Example 12—Infected Decubitus Ulcera

Fourteen elderly patients with a total of 18 decubitus ulcers on their heels or lower back were included in this study. Ulcers were rinsed thoroughly with saline and emptied as much as possible and irrigated with 5 ml, krill poly-enzyme preparation dissolved in saline (5 Casein Units/ml). The ulcers were then covered with semi-occlusive dressing. The procedure was repeated twice daily for 7 days and ulcera were inspected for inflammation, erythema, heat, swelling, necrotic tissue, pus, pain and possible adverse reactions.

Infections were gone within 4 days of treatment. Six wounds healed completely within 7 days, and a total of eleven have healed within 14 days. Seven wounds did not heal probably due to the overall condition of the patients, but the wounds showed some progress. No adverse reactions were observed.

Example 13—Fistulae Infections

The purpose of the study was to investigate the effectiveness of isolated, krill multifunctional enzyme and the krill poly-enzyme preparations in treating anal fistulae. Prior to use, one ampoule of the isolated multifunctional enzyme was reconstituted in 5 ml of hydrogel to a final concentration of 3 Casein-Units/ml. The poly-enzyme preparation was reconstituted in hydrogel to a final concentration of 5 Casein-Units/ml.

The fistulae were rinsed with sterile solution and emptied as far as possible, and then irrigated with hydrogel containing isolated multifunctional enzyme or poly-enzyme preparation. The procedure was repeated once daily and patients were inspected for erythema, heat, swelling, pus, pain and adverse reactions. The treatment continued until all signs of infection and inflammation were gone, but for no longer than 10 days. For each gel preparation, two patients with anal fistulae, with no passages to rectum, were used and treated with isolated protease and poly-enzyme preparation, respectively. For both sets of patients, total pain relief was reported within 48 hours and all signs of infections and inflammations were gone after 4 days. All fistulae were healed between day 6 and day 9, and no recurrence was reported within 6 months of follow-up. No adverse reactions were observed.

Example 14—Athlete's Foot (Epidermophytosis)

The purpose was to study the effectiveness of krill poly-enzyme preparation treating epidermophytosis of the foot. Forty-one patients with fungal infections were included in this study. Patients soaked their feet for thirty minutes once a day for three successive days in an aqueous solution contain 5 Casein Units/ml of multi-enzyme preparation for 30 minutes. Also, a hydrogel containing 5 Casein Units/ml of the krill poly-enzyme preparation was applied to the affected areas each evening immediately before bedtime for 7 nights.

The pain relief was instant in many patients and pain was totally gone within 2 days for others. Plaques over open surfaces, in cracks and under nails were readily removed by the protease and all signs of plaque, smell and infections were gone after three days.

Example 15—Foreskin Infection

The purpose was to study the effectiveness and the krill poly-enzyme preparation in treating foreskin infections in infants. Two infants, 4 resp. 6 weeks old, were treated twice daily with a solution of multi-enzyme preparation containing 1 Casein Unit/ml. 10 ml of the solution was flushed under the foreskin morning and evening, using a standard syringe with a soft catheter. After 3 days both the infants were free from symptoms and the infections did not recur during a 2 month follow-up.

Example 16—Prepuce Infections in Dogs

Six dogs with foreskin infections were flushed under the prepuce once daily with a solution of poly-enzyme preparation containing 1 Casein Unit/ml. A soft silicone catheter attached to a syringe was inserted under the foreskin and used to slowly flush the affected area with 10 ml of the poly-enzyme solution. Approximately 1 ml of the solution was kept under the foreskin for minimum of 2 minutes and the dogs were kept from licking the affected area for 30 minutes. Purulent exudation stopped within 2 days in all the cases and all signs of infection and inflammation were gone within 4 days.

Example 17—Boils in Dogs

Three boxers with painful, infected and excudating/bleeding boils between the toes were treated twice daily with poly-enzyme solution. A gauze was soaked with 2 ml of a solution of poly-enzyme preparation (5 Casein Units/ml) and then applied over the boil. The paw was bandaged to keep the gauze fixed in place and a rubber boot was used to protect the dressing. Apparent relief from pain was observed after 1 day of treatment. The flow of exudant or blood stopped within two days. After 5 to 7 days of treatment, inflammation was substantially reduced, and after 11 to 15 days, all indications of boils were gone.

Example 18—Urinary Bladder and Urethra Infections

Twelve female patients with painful urinary infections were included in this study. Before use, 6 ampoules of krill poly-enzyme preparation were reconstituted in 50 ml saline to a final concentration of 3 Casein-Units/ml.

At the start of treatment, the first discharge of urine from all patients was very turbid and the second discharge was clear to weakly turbid. Patients were treated by instillation 2 times daily. Pain relief was instant and improved ability to retain urine was obvious after two days of treatment. Microorganism (MO) samples confirmed no bacteria after 4 days of treatment and all treatments were terminated after 4 days. No adverse reactions were observed.

Figure 6:
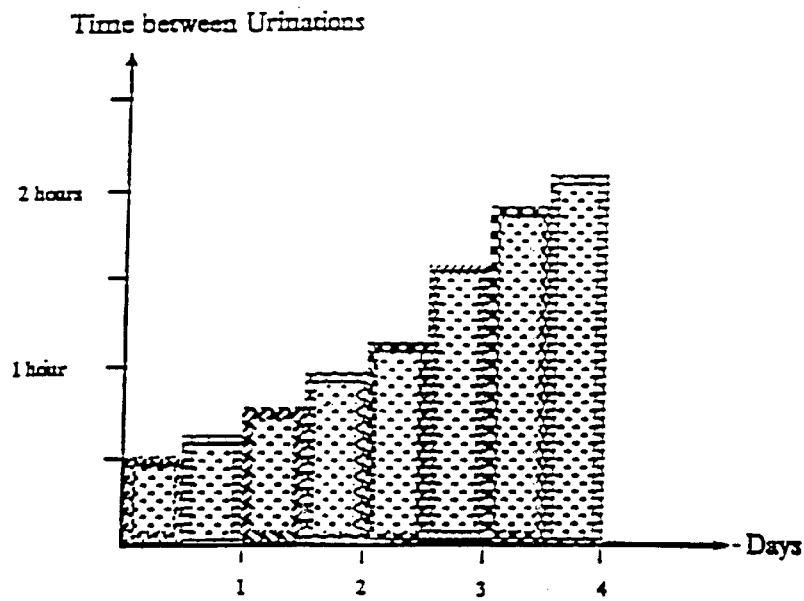
FIG. 6 shows the increase in time between urinations for urinary bladder infection patients treated with the multifunctional enzyme.

The results are summarized in FIG. 6. The average MO-status values are shown in the table below.

|  | BEFORE TREATMENT | DAY 2 | DAY 4 |
| --- | --- | --- | --- |
| MO Status: (average) | $1.4 \times 10^4$ | $4.3 \times 10^3$ | $<1.0 \times 10^2$ |
| Relative MO Status: (% of initial status) | 100% | 31% | 1% |

Example 19—Eye Infections

Fifteen patients with purulent eye infections were treated twice daily with eye-drops of the poly-enzyme preparation from krill. Before use, one ampoule of poly-enzyme preparation was reconstituted in 25 ml water to a final concentration of 1 Casein-Unit/ml. The infected eye was treated morning and evening with two drops, approx. 0.4 ml, of the solution. At each application, the eye was inspected for erythema, swelling, pus, lacrimal secretion and possible adverse reactions. The patient was treated until all signs of infection were gone, but not for longer than 10 days.

All patients were free from infections within 3 days of treatment. Erythema and swelling around the eyes faded away within 2 days and excess lacrimal secretion ceased within 2 days. After the first application all patients experienced a smoothing feeling in the infected eye and irritation and tenderness around the eyes disappeared within a few minutes. No adverse reactions were reported.

Example 20—Gum Infections

Twenty-two patients with a cute or chronic gum infections/inflammations were included in this study. Three times a day (morning, mid-day and evening) an ampoule of poly-enzyme preparation was reconstituted in 5 ml tap water (yielding 5 Casein units/ml) and used to rinse a patient's mouth cavity for 5 minutes. No eating and drinking within 2 hours after treatment was allowed. The treatment went on for 7 days independent of results.

Pain relief was reported after 20 minutes to 12 hours of treatment. Infections and inflammation s vanished within 4 days and did not reoccur during a follow-up period of 3 weeks. No adverse reactions were reported.

Example 21—Viral Infections In The Upper Airways

Eleven patients with Influenza Virus infections and secondary bacterial infections in the upper airways (e.g. sinusitis) were included in this study.

Viral infections in the lungs cause harm to lung cilia and inflammatory reactions that lead to erythema, swelling and increased mucus-secretion. The harmed cilia can no longer wipe away inhaled bacteria. Thus, bacterial infections are often secondary complications. Viruses are dependent on host-cells for their survival and multiplication and it is a difficult task to kill a virus without harming or killing the host-cell. Prior to treatment, an ampoule of isolated, krill multifunctional enzyme preparation was reconstituted in 5 ml of saline to a final concentration of 5 Casein-Units per ml.

Approximately 0.25 ml of this solution was sprayed in each nostril and the mouth-cavity was rinsed for 5 minutes with approx. 4.5 ml. The procedure was repeated three times daily and erythema, swelling, mucus-secretion, pain and adverse reactions were recorded once daily.

The treatment was continued until all signs of infection were gone but not for longer than 10 days. 8 patients were free from symptoms after 6 days of treatment and the remaining three patients after 9 days. Pain relief was experienced by all patients and occurred within 2 hours to two days. Sputum became clear within three days in patients with purulent discharges. Erythema and swelling disappeared within 4 days.

Figure 7:
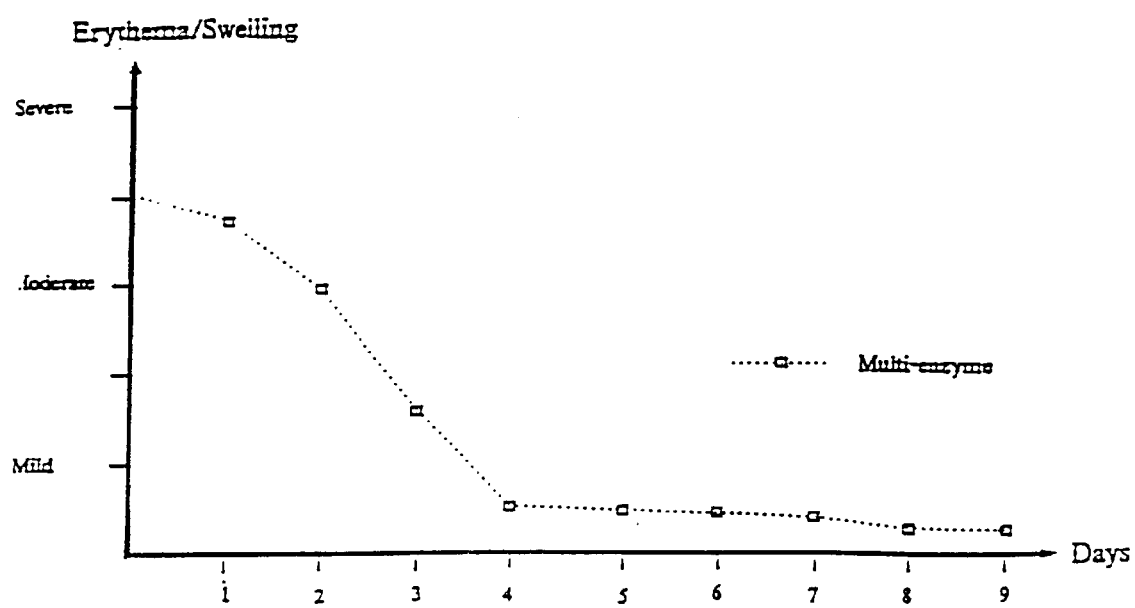
FIG. 7 shows the reduction in erythema/swelling in patients with viral lung infections treated with the multifunctional enzyme.
Figure 8:
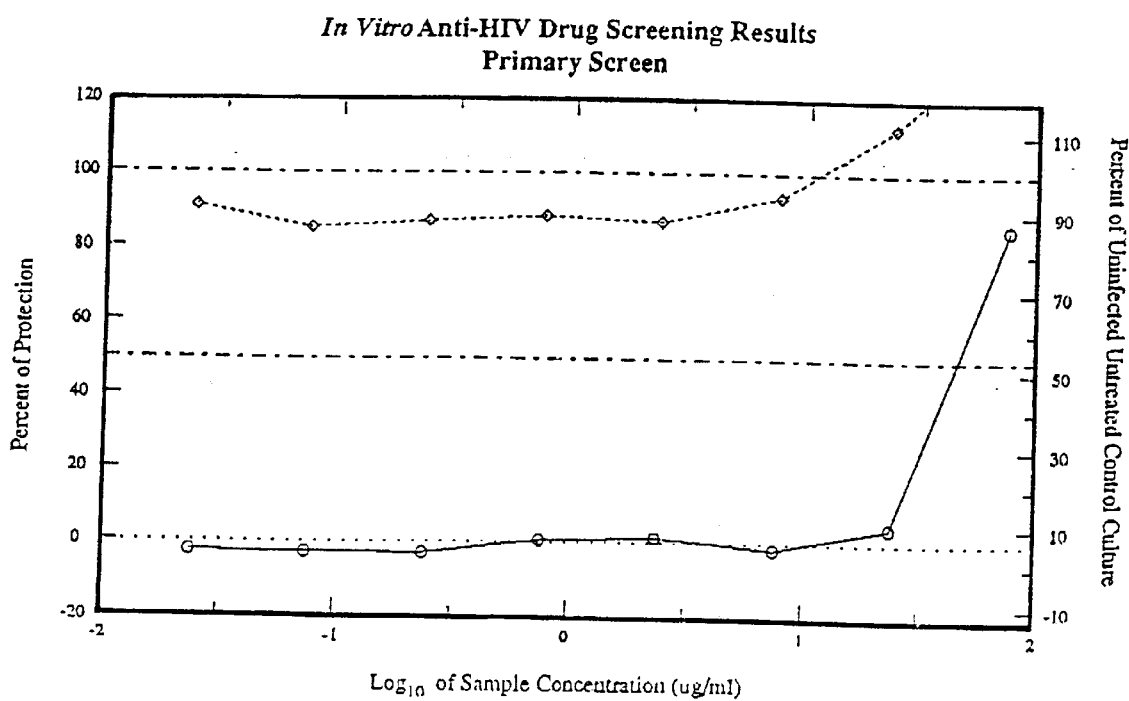
FIG. 8 shows the protective effect of the krill multifunctional enzyme against HIV.

The results are summarized in FIG. 7. No adverse reactions were observed.

Example 22—Hemorhilus Influenza

A woman of 34 had recurring sinusitis caused by infection of Hemophilus influenza. A few hours after the appearance of the symptoms of pressure and pain in the nasal sinus, her mouth was washed for 3 minutes with 4.5 ml of a 5 mg/ml solution of isolated, krill multifunctional enzyme and about 0.5 ml of the enzyme solution was sprayed into each of her nostrils. This combined treatment was repeated three times at 2 hour intervals. After which, the spray treatment was repeated every three hours for a total of 3 days. The pressure caused by the nasal sinus infection disappeared within a few hours after the first treatment and the flow of nasal secretions strongly increased. After 3 days of treatment the woman was free of complaints.

Example 23—Bronchitis

A 55 year old man having severe bronchitis complaints was treated. The man had respiration complaints, difficulty in walking more than 100 meters, severe tiredness, and a chronic hacking cough. His physician believed his bronchitis was caused by a mycoplasma which had first infected the patient 3 years earlier and which had developed antibiotic resistance. The infection led to the formation of water in the pleura, as was verified by X-ray examination.

The patient was treated with mouth washes containing about 4 mg/ml saline of isolated, krill multifunctional enzyme. The protease solution was kept in the mouth for about 4 minutes and then it was slowly swallowed. This treatment was repeated on every alternative day for the first two weeks of treatment. Also during this time, small amounts (0.5 ml) of an aerosol of the protease solution was inhaled.

During the first two weeks no improvement was observed. After two weeks treatment the lymph gland on the left side of the patient's neck swelled, resulting in pain. Following this, the treatment was repeated about 3 times. About 1.5 weeks after this, the lymph node swelling had disappeared and the bronchitis complaints of the patient began to subside. After a further 3 weeks of treatment with mouth washes on every fourth day the bronchitis complaint had disappeared. After a treatment extending over 6.5 weeks the patient had recovered completely, and after a short time he could walk substantial distances without problems.

Example 24A—Gastric Ulcer

A man of 40 having recurring complaints characteristic of a mild form of gastric ulcer was treated with acid-resistant gelatin capsules containing 5 mg of krill poly-enzyme preparation per capsule. No filler was added to the encapsulated preparation. The patient swallowed 1 capsule a day with a glass of water for 2 weeks. After about 4 days the stomach complaints disappeared and the patient's intestines functioned normally.

A 55 years old man having recurring gastric ulcer complaints over 20 years was treated with the same dosage described above. After a few day's treatment the complaints had disappeared and his intestines worked normally.

Gastric ulcer is an inflammatory process that is often due to a bacterial attack. First the intestinal mucosa is infected by the microbe, leading to inflammation. Many believe the inflammation associated with ulcers is involved in the etiology of some autoimmune diseases.

Example 24B—Colitis Ulcerative

The patient had a fifteen year medical history of C. Ulcerative, which had been treated with the antiphlogistic Salazopyrine (Pharmacia, Sweden). For six weeks she swallowed once daily an acid resistant capsule containing 1 mg of lyophilized krill multifunctional enzyme. Concurrently she maintained her Salazopyrine treatment. Two hours after her first treatment with the multifunctional enzyme, she experienced an attack of gastric pain, gas and diarrhea and these symptoms remained for approximately six hours. After her second treatment she experienced slight pain for about 30 minutes. After this, she experienced no further adverse reactions. On days 16 and 29 she experienced gastric pain and diarrhea in connection with unusual meals. However, these episodes where shorter and less severe than her previous episodes. Through the course of the treatment, she recorded improved comfort. During the 3–4 months following treatment, her symptoms slowly returned to the severity reported pre-treatment.

Example 25—Herpes Genitalis

A man of 62 having a long established case of Herpes genitalis was treated. Outbreaks recurred regularly every 4 months, and during acute outbreaks the man abstained from sexual intercourse.

During an acute outbreak, the affected area was bandaged with a bandage soaked with a solution of isolated, krill multifunctional enzyme until it contained 3 mg of enzyme. The bandaging treatment was repeated twice a day for 2 days. His complaints disappeared after the second treatment. The man had no outbreaks during the 10 months following treatment.

Example 26—Herpes Simplex Infection In The Mouth Cavity

Eight patients with relapsed Herpes Simplex blisters in the mouth cavity were treated twice daily with mouth-wash. Prior to use, each ampoule of krill poly-enzyme preparation was reconstituted in 5 ml of saline to a final concentration of 5 Casein-Units/ml. The patient rinsed his or her mouth cavity with the solution for 5 minutes. No eating or drinking was allowed within 2 hours after each treatment. The procedure was repeated twice daily and clinical parameters, erythema, swelling, pain and adverse reactions were recorded once daily. The treatment was continued until all signs of infection were gone, but not for longer than 10 days.

Pain relief was experienced within 2 hours after the first treatment. In some patients the pain recurred between treatments during the first two days, but never thereafter. After 5 days, all patients were free from symptoms and all blisters had healed. No adverse reactions were observed.

Example 27—Herpes Zoster

A 70 year old man who had had a very painful Herpes Zoster infection in his face for 10 months was treated topically with a gauze bandage soaked to absorb a solution containing 1–2 mg of krill poly-enzyme preparation every three days. After the first treatment the itch and pain were reduced. The pain disappeared completely after 12 days. Due to the pain associated with the infection, the man had had difficulties in chewing, but after 12 days he was able to chew food with no problems.

Example 28—Acne

Two women, aged 29 and 30 years, were treated for facial acne. The 29 year old woman had severe acne, whereas the 30 years old woman had moderate acne.

The patients were treated with 0.1 mg of isolated, krill multifunctional enzyme several times a day for 4–6 days by applying 0.5 g/cm$^2$ to 2 g/cm$^2$ of a hydrogel containing 5 mg/ml of krill multifunctional enzyme. Improvement was apparent after the first treatment, and after a week of treatment only pigment traces of the acne were evident.

Example 29—Psoriasis and Dry Eczema

Psoriasis plaques and dry eczema plaques were readily decomposed with hydrogel preparations of the isolated, krill multifunctional enzyme. 0.5 g/cm$^2$ of hydrogel containing 5 Casein Units/ml enzyme was applied to the sites in need of treatment and the site was covered with a semi-occlusive dressing. The treatments were repeated two times daily. Within 24 hours the plaques were completely gone and the sensitive skin, especially in psoriasis patients, showed reduced inflammation. Following treatment, the affected areas were responsive to steroid creams.

Example 30A—Eczema Infections

The purpose was to study the effectiveness and usefulness of the krill poly-enzyme preparation in treating eczematous seborrheic and psoriasis infections. Forty patients were treated once to twice daily with multi-enzyme hydrogel containing 2.5 Casein Units/ml of the poly-enzyme preparation.

Patients with dry eczema/plaque showed no signs of inflammation or infection after 2–4 treatments. The fatty type of seborrheic plaques disappeared after 6–9 days, though the associated inflammations/infections had vanished within the initial 2–4 days of treatment. Patients with psoriasis plaque experienced an improved responsiveness to steroid creams, probably due to removal of plaque by the multi-enzyme preparation, resulting in better access to the skin.

Example 30B—Lichen Planus—With Associated Infection

The patient suffered from Lichen Planus of the lower gum. The affected areas showed papules and lesions, and were covered yeast plaque. Each day at that time 1 g of a hydrogel containing 0.5 mg/ml of krill multifunctional enzyme was applied to the affected areas. After three days, the plaques and papules were gone. On day 7, all lesions were healed and the treatment was stopped.

Example 31—Thrombolytic/anti-embolic Properties

The purpose of the study was to investigate the efficacy of isolated krill multifunctional enzyme in the treatment of thrombi and emboli. Thrombi were caused by applying an artificial stasis to the main ear vein of a rabbit until a proper thrombus had developed. Protease was injected (0.5 mg dissolved in 0.2 ml of isotonic solution), into the ear vein in the direction of the thrombus, at a location 2 cm from the ischemic area. Within 30 minutes the thrombus had completely dissolved and the blood had free passage. Small necroses developed in the treated area but these were resorbed within 7 days. In the control animals the ischemic area turned necrotic within 4–5 days.

Example 32—Dental Plaque in Dogs

The purpose of this study was to investigate the effectiveness of krill poly-enzyme preparation in removing dental plaque. A dog model was used. Before use, each ampoule of the poly-enzyme preparation was reconstituted in 5 ml of saline to a final concentration of 5 Casein-Units/ml.

The content from a freshly prepared ampoule was carefully painted over teeth and gingiva. The tongue was fixated for minimum 2 minutes and food and beverage were not allowed for 2 hours post-treatment. The treatment was repeated twice daily until all plaque was completely decomposed. The dogs were inspected for status of plaque, saliva secretion and adverse reactions once daily.

Eight beagles with abnormal plaque formation due to special feeding and housing were included in this study. After 4 days all signs of plaque were gone and the study was terminated. No adverse reactions could be observed.

Example 33—Human Dental Plaque

The purpose of this study was to investigate the efficacy of krill poly-enzyme preparation in removing dental plaque. One ampoule of poly-enzyme preparation was reconstituted in 5 ml of saline to a final concentration of 5 Casein-Units/ml.

An ampoule of poly-enzyme solution was prepared before each treatment and used to rinse the patient's mouth cavity for 5 minutes. Food and beverage were not allowed for 2 hours post-treatment. The treatment was repeated twice daily and the patients were inspected once daily for plaque, saliva secretion, dryness, and adverse reactions. The patients were not allowed to brush their teeth during the study period. The treatment was continued until all signs of plaque were gone, but not for longer than 7 days.

Two hours after the first treatment all patients experienced a soft and smooth sense over their teeth. Visual inspection showed remnants of plaque. 2 hours after the third treatment, all signs of plaque were gone and treatments were terminated. No adverse reactions were observed.

Clinical Example 34—Cancer

The purpose of the study was to investigate the efficacy of the krill poly-enzyme preparation in treating Yoshida Sarcoma tumor cells in juvenile rats. Yoshida sarcoma cells are described, for instance, in Micotina et al., *Tumour Biology*, 12: 225, 1991, and Goseki et al., *Cancer*, 69: 1865, 1992. The poly-enzyme preparation was administered by three different routes (intraperitoneally (i.p.), intratumorally (i.t.) and subcutaneously (s.c.)) to white Wistar rats that had been implanted Yoshida Sarcoma cells. The treatment groups were as follows:

A. A single administration i.p. of 5 mg/kg.
B. A single administration i.t. of 5 mg/kg.
C. A single administration s.c. of 5 mg/kg.
D. Twice daily administration s.c. of 1.25 mg/kg for seven days.
E. S.c. administrations of 5 mg/kg on four alternating days.
F. S.c. administrations of 12.5 mg/kg on four alternating days.

The krill poly-enzyme preparation was stored as a lyophilized white powder without preservatives or antimicrobial additives. Before use, the white powder was reconstituted in isotonic saline at a concentration of 5 mg/ml solution. $1\times10^4$ Yoshida Sarcoma cells were implanted subcutaneously on the back of white Wistar rats. When the implanted cells had generated a 10 mm×10 mm tumor, the rats were either treated with poly-enzyme preparation or used as untreated controls. The rats were sacrificed 7 days after the last treatment. The size of the tumors was measured and compared with the tumors of untreated control rats.

The relative reduction of the size of the tumor was 46% for group A, 56% for group B and 49% group C. In the group treated with repeated doses of 1.25 mg/kg twice a day over 7 days (group D), the reduction was 72%. In the groups receiving 5 mg/kg and 12.5 mg/kg s.c. every second day (groups E & F), the tumor reductions were 53% and 69%, respectively. In all treated rats, the portion of the tumors that was necrotic was substantially higher than for tumors from untreated rats. Also, the treated rats gained weight more rapidly than did untreated rats.

One rat in the group receiving 12.5 mg/kg every second day showed an absolute loss of tumor mass (rather than a relative loss). The degree of metastasis in the treatment groups was very small compared to the control rats. The treated rats showed normal behavior regarding drinking and eating, in contrast to the control rats, which were subdued and exhibited no appetite. No adverse reactions could be observed during this trial.

Example 35—Anti-viral Effect on HIV-contaminated Cell Lines, in vitro

The krill multifunctional enzyme was tested for anti-HIV using the National Cancer Institute's standard assay. See Weislow et al., J. Natl. Cancer Inst. 81:577–586, 1989. Briefly, the procedure comprises:

(1) The multifunctional enzyme was dissolved in dimethyl sulfoxide, diluted 1:100 in cell culture medium, and then subjected to serial dilutions. Virus infected T4 lymphocytes (CEM cell line) were added to the various dilutions. Matched controls comprise uninfected cells treated with the enzyme for HIV-infected cells parallelly treated without the presence of the multifunctional enzyme.

(2) The cell cultures were incubated at 37° C. under 5% carbon dioxide atmosphere for 6 days.

(3) Tetrazolium salt, XTT, was added to the culture wells, and the cultures were incubated to allow color development by viable cells. Four of the cultures were analyzed spectrophotometrically and microscopically to quantitate the number of viable cells present. FIG. 20 shows an illustrative run of the assay. Line A is for the cells treated with multifunctional enzyme, while Line B is the untreated control. No activity is seen until concentrations in excess of 10 μg/ml, at which point a sharp transition in activity occurs and the enzyme begins to show near total protective activity. The concentrations at which the enzyme shows substantial protection are at least ten-fold less than the blood serum concentrations known to be safe.

For each of Examples 7–35, the krill multifunctional enzyme is substituted with the multifunctional enzyme from another source and is comparably effective.

EXAMPLE 36

Multifunctional Enzyme Purification

A 100 kg of frozen antarctic Krill were thawed, and mixed with 100 kgs of distilled water, and stirred for 30 minutes. The krill used were harvested in the January through March period. During this period, krill are largely without pigment and are called "white" krill. (Due to dietary changes, later in the season krill are harvested as "red" krill. Multifunctional enzyme yields from red krill are 30 to 40% less than from white krill. Still later in the season, during June through August, "black" krill are harvested. Black krill yield still less enzyme.) The supernate was collected by centrifugation using a GL-sieve, starch centrifuge (Model 220, available from G. Larssons Mekaniska Verkstad, Fjälkinge, Sweden) using a 125 micron spinning cone at 1,000 rpm. The pH of the supernate was adjusted to 6.2. The supernate had a turbidity of less than 4% and a fat content of less than 2%.

The supernate was further clarified by centrifugation at 17,000 xg and mixed with 5 kgs of DEAE-sepharose gel (Pharmacia, Sweden), which had been previously been equilibrated to pH 6.2. The mixture was stirred gently for 1 hour. The gel was collected on a filter bed and washed with 5 volumes of 0.4 M NaCl. The gel was then packed into a suitable column container using the same saline solution. The column was then washed overnight with 15 bed volumes of 0.4 M NaCl.

A protein containing fraction (approximately 1.5 liters collected) was desorbed from the gel with 0.6 M NaCl. This fraction contained multiple proteins with molecular weights ranging from 10 kd to greater than 90 kd, as determined by SDS-PAGE. The protein content was 20 g/l, as determined by absorbance at 280 nm. The protein fraction was filter sterilized through a 0.20 micron filter and applied to an affinity column comprising soybean trypsin inhibitor coupled to agarose (200 ml of gel, substitution ratio 3:1 gel:inhibitor). The affinity gel was washed with 4 bed volumes of 1 M NaCl. The multifunctional enzyme was desorbed from the gel with 0.2 M sodium citrate, pH 3.0. (in parallel procedures, equivalent preparations of a multifunctional enzyme were prepared by using either 0.5 M TRIS-HCl, pH 8.0 or 0.1 M ammonium solution, pH 11 to desorb the multifunctional enzyme). The yield of multifunctional enzyme was 100 mg.

The multifunctional enzyme preparation was adjusted to pH 7.4 and applied to 200 ml of an agarose affinity gel to which a prior preparation of the multifunctional enzyme had been coupled (6:1 substitution ratio gel:enzyme). This step was applied to assure the removal of any contaminating protease inhibitor.

The purified multifunctional preparation was homogeneous by SDS-PAGE. The purified preparation was filter sterilized and alloquoted into injection vials. The injection vials were freeze dried. The freeze-dried powder is stable when stored at 4° C.

EXAMPLE 37

Protein Characterization

The multifunctional enzyme was purified by the protocol described above in Example 36. For the three preparations, the multifunctional protease was eluted from the trypsin inhibitor gel with buffer at pH 3, pH 8, and pH 11, respectively. These preparations shall be termed "Prep-3," "Prep-8," and "Prep-11." These preparations were dissolved in water to a concentration of 6 mg/ml.

Samples of each preparation were analyzed by SDS-PAGE, and each preparation was found to contain a single protein that banded with apparent molecular weight of 29 kd. The SDS bands were electroblotted onto PVDF membranes and sequenced through 25 cycles of Edman degradation. See, Matsudaira, J. Biol Chem., 262: 10035–10038, 1987. Each preparation yielded the identical sequence shown below:

I V G G M/N E V T P H A Y P W Q V G L F I D D M Y F (SEQ ID NO:17).

Figure 9:
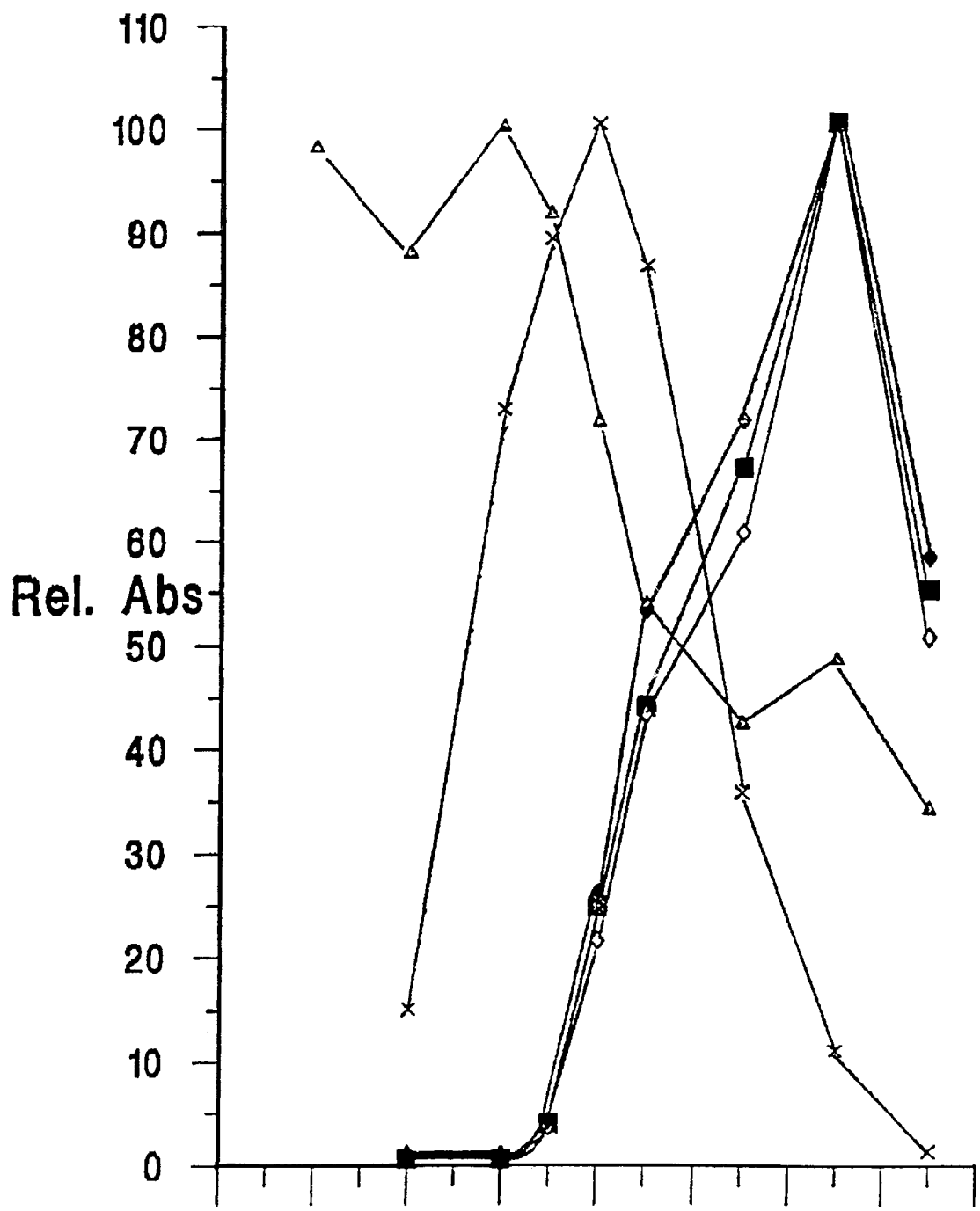
FIG. 9 shows the pH dependence of the krill multifunctional enzyme when tested against different substrates.

Accordingly, it is clear that all three preparations are homogenous, although each is micro-heterogeneous at position 5, probably reflecting the presence of two highly related genes for the enzyme. The proteolytic activity of each of the three preparations was tested against substrate benzoyl-valgly-arg-p-nitroaniline. Hydrolysis of this substrate can be monitored at 210 nm, reflecting the release of p-nitroaniline. The pH-dependence of the three preparations at an ionic strength of 0.1 M is shown in FIG. 9. The profile for Prep-3 (shown with filled squares), Prep-8 (shown with open diamonds) and Prep-11 (shown with filled diamonds) are identical. All three had a pH optimum for this substrate of 9.5.

With the elastase substrates succinyl-p-ala-pro-ala-p-nitroanilide and boc-ala-ala-pro-ala-p-nitroanilide, the pH optimum for Prep-8 was 7.0. See the profile in FIG. 9, represented by the X's. Similar model substrate studies determined that the order of cleavage efficiencies for the krill multifunctional enzyme is chymotrypsin≧trypsin≧elastase.

For the substrate azocasein, the profile for pH dependence was broad and surprisingly in the acidic pH region. See the profile in FIG. 9, represented by the open triangles.

$K_m$ values were determined using benzoyl-pal-gly-arg-p-nitroanilide in 0.1 M in CAPS buffer containing 2 mM $Ca^{++}$ at pH 9.5. The $K_m$ values for Prep-3, Prep-8 and Prep-11 were 210±8, 210±8 and 230±13 μM, respectively. Against the substrate succinyl-ala-ala-pro-phe-p-nitroanilide, under the same conditions, the $K_M$ values were 260±50, 270±50 and 270±40 μM, respectively.

The effectiveness of three protease inhibitors was tested against the three enzyme preparations. The results, determined at pH 9.5, were as follows:

|  | Prep-3 | Prep-8 | Prep-11 |
| --- | --- | --- | --- |
|  | (% ACTIVITY REMAINING) | | |
| Antipain (1 μM) | 2 | 5 | 5 |
| Chymostatin (1 μM) | 0 | 0 | 0 |
| Bovine pancreatic trypsin inhibitor (1 μM) | 2 | 1 | 1 |

The effectiveness of other protease inhibitors against Prep-8 was tested in a 0.1 M Tris-HCl buffer pH 7.5. Benzoyl-val-gly-arg-p-nitroanilide ("ARG-p-NA") and succinyl-ala-pro-phe-p-nitroanilide (Phe-pNA) were used as substrates. The results were as follows:

| | Substrate: | |
| --- | --- | --- |
| Inhibitor: | Phe-pNA | Arg-pNA |
| | (Activity remaining, %) | |
| Phosphoramidon (10 μM) | 94 | 87 |
| Elastatinal (10 μM) | 100 | 100 |
| Eglin C fragment (8.4 μM) | 100 | Not done |
| Anti-Thrombin III (0.2 μM) | 2 | 4 |
| α-anti-chymotrypsin (0.2 μM) | 1 | 7 |
| α-proteinase inhibitor (0.2 μM) | 0 | 0 |

Figure 10:
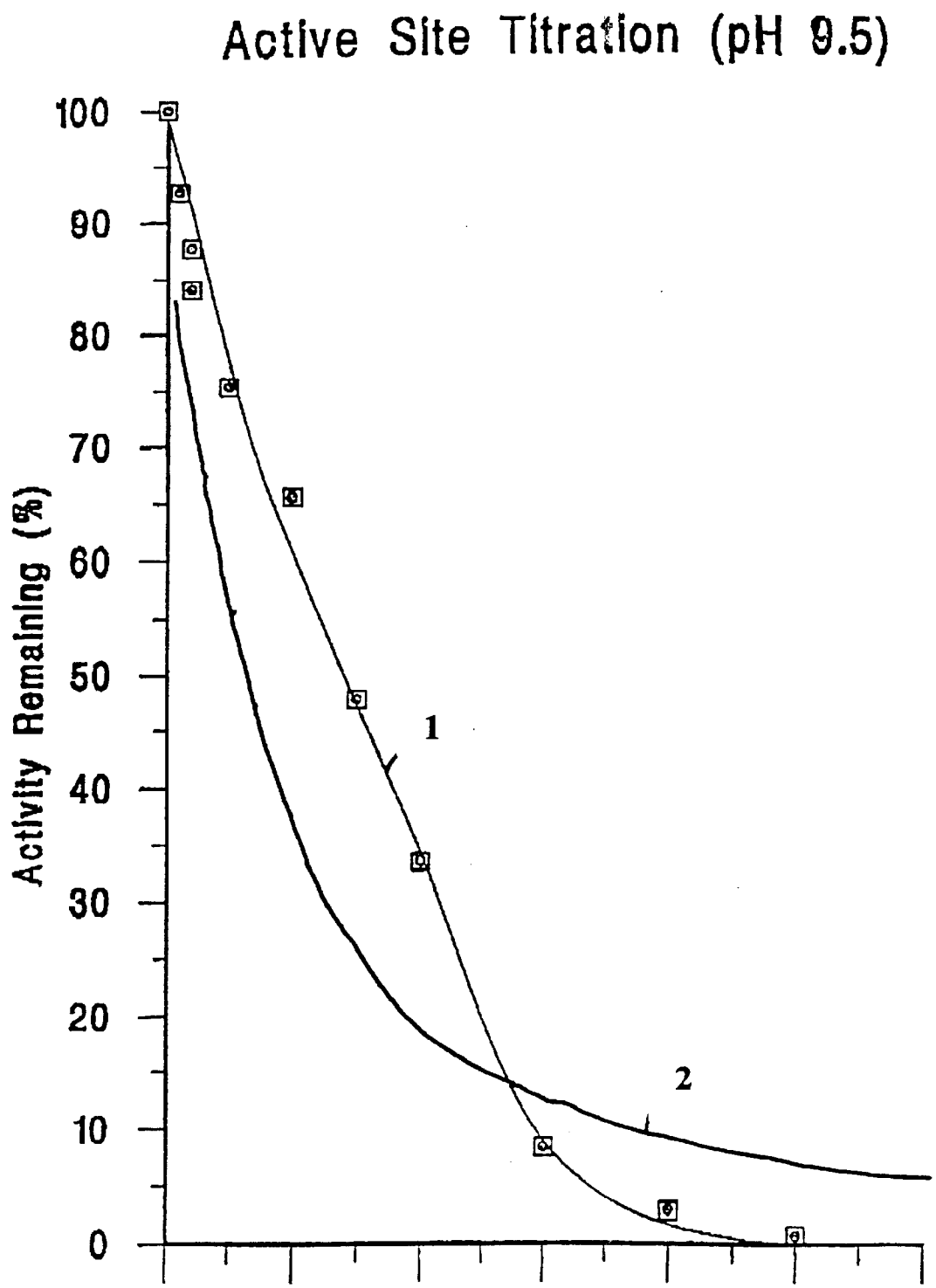
FIG. 10 shows the titration of the activity of the krill multifunctional enzyme with 2 different protease inhibitors.

Aliquots of a solution of Prep-8, with a nominal concentration of 6 mg/ml, were titrated against either bovine pancreatic trypsin inhibitor, $α_1$-antichymotrypsin, α-protease inhibitor and soybean trypsin inhibitor. The results are displayed in FIG. 10. Profile 1 is for a titration of bovine pancreatic trypsin inhibitor tested at pH 9.5 using benzoyl-val-gly-arg-p-nitroanilide as the substrate. For profile 2, the pH was 7.0 and the substrate used was succinyl-ala-ala-pro-phe-p-nitroanilide. Similar profiles have been done with α-antichymotrypsin, α-protease inhibitor and soybean trypsin inhibitor. These curves can be used to estimate the $K_i$ for the inhibitor and the effective concentration of multifunctional enzyme.

What is claimed is:

1. A method of treating wounds comprising topically administering a composition consisting essentially of, with respect to proteases, krill derived multifunctional enzyme, wherein a wound treating effective amount of multifunctional enzyme is administered and wherein the multifunctional enzyme has endo and exo peptidase activity, a molecular weight of 26,000–32,000 as determined by SDS PAGE and an N-terminal sequence comprising:

I-V-G-G-X-E-V-T-P-H-A-Y-P-W-Q-V-G-L-F-L-D-D-M-Y-F (SEQ ID NO: 17)

wherein X is any amino aid.

2. The method of claim 1, wherein the enzyme has at least two endopeptidase activities selected from the group consisting of chymotrypsin, trypsin, collagenase and elastase activities.

3. The method of claim 1, wherein the enzyme has at least three of said endopeptidase activities.

4. The method of claim 1, wherein the enzyme has at least four of said endopeptidase activities.

5. The method of claim 1, wherein enzyme has an apparent molecular weight of about 29,000.

6. The method of claim 1, wherein the enzyme has an isoelectric point of approximately 4.0.

7. The method of claim 1, wherein the enzyme has the ability to release free amino acids from casein.

8. The method of claim 7, wherein the enzyme has trypsin and chymotrypsin activity.

9. The method of claim 7, wherein the enzyme has trypsin and collagenase activity.

10. The method of claim 7, wherein the enzyme has chymotrypsin and collagenase activity.

11. The method of claim 7, wherein the enzyme has trypsin, chymotrypsin and collagenase activity.

12. The method of claim 7, wherein the enzyme has trypsin, chymotrypsin, collagenase and elastase activity.

* * * * *